US005874291A

United States Patent [19]

Bielefeldt et al.

[11] Patent Number: 5,874,291

[45] Date of Patent: Feb. 23, 1999

[54] DEGRADATION OF ENVIRONMENTAL TOXINS BY A FILAMENTOUS BACTERIUM

[75] Inventors: Angela R. Bielefeldt, Ames, Iowa; H. David Stensel, Mercer Island, Wash.; Stuart E. Strand; Russell P. Herwig, both of Seattle, Wash.

[73] Assignee: University of Washington, Seattle, Wash.

[21] Appl. No.: 642,229

[22] Filed: Apr. 30, 1996

Related U.S. Application Data

[63] Continuation-in-part of Ser. No. 599,867, Feb. 12, 1996, abandoned, which is a continuation of Ser. No. 246,865, May 20, 1994, abandoned.

[51] Int. Cl.[6] .............................. B09B 3/00; C12P 1/04; C02F 3/34; C12N 1/20

[52] U.S. Cl. .............................. 435/262; 435/42; 435/170; 435/252.1; 435/262.5; 435/264

[58] Field of Search .............................. 435/262, 262.5, 435/264, 170, 42, 252.1

[56] References Cited

U.S. PATENT DOCUMENTS

| | | | |
|---|---|---|---|
| 3,719,675 | 3/1973 | Baker et al. | 544/167 |
| 4,713,343 | 12/1987 | Wilson, Jr. et al. | 435/264 |
| 4,833,086 | 5/1989 | Horowitz | 435/252.1 |
| 4,925,802 | 5/1990 | Nelson et al. | 435/262 |
| 5,024,949 | 6/1991 | Hegeman et al. | 435/262 |
| 5,071,755 | 12/1991 | Nelson et al. | 435/167 |
| 5,120,652 | 6/1992 | Groeger et al. | 435/822 |
| 5,196,339 | 3/1993 | Hanson et al. | 435/262 |
| 5,512,479 | 4/1996 | Steffan | 435/262.5 |

OTHER PUBLICATIONS

Alvarez–Cohen, L., and McCarty, P.L., "A Cometabolic Biotransformation Model for Halogenated Aliphatic Compounds Exhibiting Product Toxicity," *Environ. Sci. Technol.,* 25:1381–1386, 1991.

Alvarez–Cohen, L., and McCarty, P.L., "Effects of Toxicity, Aeration, and Reductant Supply on Trichloroethylene Transformation by a Mixed Methanotrophic Culture," *App. and Environ. Microbiol.,* 57:228–235, 1991.

Alvarez–Cohen, L., and McCarty, P., "Product Toxicity and Cometabolic Competitive Inhibition Modeling of Chloroform and Trichloroethylene Transformation by Methanotrophic Resting Cells," *App. and Environ. Microbiol.,* 57:1031–1037, 1991.

Broholm, K., et al., "Different Abilities of Eight Mixed Cultures of Methane–Oxidizing Bacteria to Degrade TCE," *Wat. Res.,* 27:215–224, 1993.

Dalton, H., and Stirling, D.I., "Co–metabolism," *Phil. Trans. R. Soc. Lond.,* 297:481–496, 1982.

Fogel, M.M., et al., "Biodegradation of Chlorinated Ethenes by a Methane–Utilizing Mixed Culture," *App. and Environ. Microbiol.,* 51:720–724, 1986.

Folsom, B.R., et al., "Phenol and Trichloroethylene Degradation by *Pseudomonas cepacia* G4: Kinetics and Interactions between Substrates," *App. and Environ. Microbiol.,* 56:1279–1285, 1990.

Harker, A.R., and Young K., "Trichloroethylene Degradation by Two Independent Aromatic–Degrading Pathways in *Alcaligenes eutrophus* JMP134," *App. and Environ. Microbiol.,* 56:1179–1181, 1990.

Henry, S.M., and Grbic–Galic, D., "Influence of Endogenous and Exogenous Electron Donors and Trichloroethylene Oxidation Toxicity on Trichloroethylene Oxidation by Methanotrophic Cultures from a Groundwater Aquifer," *App. and Environ. Microbiol.,* 57:236–244, 1991.

Hopkins, G.D., et al., "Microcosm and In Situ Field Studies of Enhanced Biotransformation of Trichloroethylene by Phenol–Utilizing Microorganisms," *App. and Environ. Microbiol.,* 59:2277–2285, 1993.

Krumme, M.L., et al., "Degradation of Trichloroethylene by *Pseudomonas cepacia* G4 and Constitutive Mutant Strain G4 5223 PR1 in Aquifer Microcosms," *App. and Environ. Microbiol.,* 59:2746–2749, 1993.

Nelson, M.J.K., et al., "Biodegradation of Trichloroethylene and Involvement of an Aromatic Biodegradative Pathway," *App. and Environ. Microbiol.,* 53:949–954, 1987.

Nelson, M.J.K., et al., "Trichloroethylene Metabolism by Microorganisms That Degrade Aromatic Compounds," *App. and Environ. Microbiol.,* 54:604–606, 1988.

Oldenhuis, R., et al., "Degradation of Chlorinated Aliphatic Hydrocarbons by *Methylosinus trichosporium* OB3b Expressing Soluble Methan Monooxygenase," *App. and Environ. Microbiol.,* 55:2819–2826, 1989.

Shields, M.S., and Reagin, M.J., "Selection of a *Pseudomonas cepacia* Strain Constitutive for the Degradation of Trichloroethylene," *App. and Environ. Microbiol.,* 58:3977–3983, 1992.

Spain, J.C., et al., "Monohydroxylation of Phenol and 2,5–Dichlorophenol by Toluene Dioxygenase in *Pseudomonas putida* F1," *App. and Environ. Microbiol.,* 55:2648–2652, 1989.

(List continued on next page.)

*Primary Examiner*—Herbert J. Lilling
*Attorney, Agent, or Firm*—Christensen O'Connor Johnson & Kindness PLLC

[57] ABSTRACT

This invention pertains to substantially purified cultures of a gram-negative, aerobic, filamentous bacterium with cells ranging in length from 20–200 μm, that accumulates intracellular poly-β-hydroxybutyrate in intracellular granules, and that degrades chlorinated aliphatic compounds such as trichloroethylene and dichloroethylene, as well as phenol and other substituted benzenes. The invention includes the representative strain A-1, which has been deposited at the American Type Culture Collection under the accession number 55581. Also included are methods for using the new bacterium for bioremediation of contaminated environmental sites.

6 Claims, 17 Drawing Sheets

OTHER PUBLICATIONS

Stensel, H.D., et al., "Toxicity Effects of Methanotrophic Biotransformation of Trichloroethylene," *Water Env. Fed. 65th Annual Conf. & Exposition,* New Orleans, I:273:282, 1992.

Strand, S.E., et al., "Kinetics of chlorinated hydrocarbon degradation by suspended cultures of methane–oxidizing bacteria," *Res. J. WPCF,* 62:124–129, 1990.

Tsien, H.–C., et al., "Biodegradation of Trichloroethylene by *Methylosinus trichosporium* OB3b," *App. and Environ. Microbiol.,* 55:3155–3161, 1989.

Vannelli, T., et al., "Degradation of Halogenated Aliphatic Compounds by the Ammonia–Oxidizing Bacterium *Nitrosomonas europaea,*" *App. and Environ. Microbiol.,* 56:1169–1171, 1990.

Wackett, L.P., et al., "Survey of Microbial Oxygenases: Trichloroethylene Degradation by Propane–Oxidizing Bacteria," *App. and Environ. Microbi.,* 55:2960–2964, 1989.

Wackett, L.P., and Householder, S.R., "Toxicity of Trichloroethylene to *Pseudomonas putida* F1 Is Mediated by Toluene Dioxygenase," *App. and Environ. Microbiol.,* 55:2723–2725, 1989.

Zylstra, G.J., et al., "Trichloroethylene Degradation by *Escherichia coli* Containing the Cloned *Pseudomonas putida* F1 Toluene Dioxygenase Genes," *App. and Environ. Microbiol.,* 55:3162–3166, 1989.

Bielefeldt, A.R., et al., "Cometabolic Degradation of TCE and DCE Without Intermediate Toxicity," *J. of Environ. Eng.,* 791–797, 1995.

Bielefeldt, A.R., et al., "A Phenol Degrading Consortia Able to Degrade High Concentrations of TCE and DCE Without Intermediate Toxicity," *94th ASM General Meeting,* 439, 1994.

Chuba, P.J., et al., "Synthetic Oligodeoxynucleotide Probes for the Rapid Detection of Bacteria Associated with Human Periodontitis," *J. of Gen. Microbiol.,* 134:1931–1938, 1988.

Dams, E., et al., Supplement of Nucleic Acids Research by Dept. of Microbiol., University of Illinois, "Compilation of Small ribosomal Subunit RNA Sequences," *IRL Press Limited,* Oxford, England, 16:87, 93–95, 1988.

Dyksterhouse, S.E., et al., "*Cycloclasticus pugetii* gen. nov., sp. nov., an Aromatic Hydrocarbon–Degrading Bacterium from Marine Sediments," *Int'l. J. of Sys. Bac.,* 45:116–123, 1995.

Ensley, B.D., "Biochemical Diversity of Trichloroethylene Metabolism," *Annu. Rev. Microbiol.,* 45:283–299, 1991.

Göbel. U., et al., "Synthetic Oligonucleotide Probes Complementary to rRNA for Group– and Species–Specific Detection of Mycoplasmas," *Israel J. of Med. Sci.,* 23:742–746, 1987.

Gutell, R.R., et al., "Lessons from an Evolving rRNA: 16S and 23S rRNA Structures from a Comparative Perspective," *Microbiol. Rev.,* 58:10–26, 1994.

Hopkins, G.D., et al., "Trichloroethylene Concentration Effects on Pilot Field–Scale In–Situ Groundwater Bioremediation by Phenol–Oxidizing Microorganisms," *Environ. Sci. Technol.,* 27:2542–2547, 1993.

Moncla, B.J., et al., "Use of Synthetic Oligonucleotide DNA Probes for the Identification of *Bacteroides gingivalis,*" *J. of Clin. Microbiol.,* 28:324–327, 1990.

Noller, H.F., "Structure of Ribosomal RNA," *Ann. Rev. Biochem.,* 53:119–162, 1984.

Olsen, G.J., et al., "Microbial Ecology and Evolution: A Ribosomal RNA Approach," *Ann. Rev. Microbiol.,* 40:337–365, 1986.

Olsen, G.J., et al., "Minireview: The Winds of (Evolutionary) Change: Breathing New Life Into Microbiology," *J. of Bact.,* 176:1–6, 1994.

Rasche, M., et al., "Factors Limiting Aliphatic Chlorocarbon Degradation by *Nitrosomonas europaea:* Cometabolic Inactivation of Ammonia Monooxygenase and Substrate Specificity," *App. and Environ. Microbiol.,* 57:2986–2994, 1991.

Shields, M., et al., "Novel Pathway of Toluene Catabolism in the Trichloroethylene–Degrading Bacterium G4," *App. and Environ. Microbiol.,* 55:1624–1629, 1989.

Wallace, R.B., et al., "Hybridization of synthetic oligodeoxyribonucleotides to Φχ 174 DNA: The effect of single base pair mismatch," *Nucl. Ac. Res.,* 6:3543–3557, 1979.

Woese, C.R., "Bacterial Evolution," *Microbiol. Rev.,* 51:221–271, 1987.

Yabuuchi, E., et al., "Proposal of Burkholderia gen. nov. and Transfer of Seven Species of the Genus Pseudomonas Homology Group II to the New Genus, with the Type Species *Burkholderia cepacia* (Palleroni and Holmes 1981) comb. nov., " *Microbiol. Immunol.,* 36:1251–1275, 1992.

```
          1                                                  50
C. test   CGAACTATAG AGTTTGATCC TGGCTCAGAT TGAACGCTGG CGGCATGCTT
Brachym   .......... .......... ........AT TGAACGCTGG CGGCATGCTT
A-1       .......... .......... ........AT TGAACGCTGG CGGCATGCTT
Stripa    .......... .......... .......... .......... ..........

          51                                                100
C. test   TACACATGCA AGTCGAACGG TAACAGGT.C TTCGG.ATGC TGACGAGTGG
Brachym   TACACATGCA AGTCGAACGG TAACAGGTCC TTCGG.ATGC TGACGAGTGG
A-1       TACACATGCA AGTCGAACGG CAGCATGGGC TTCGGCCTGA TGGCGAGTGG
Stripa    .......... .......... .......... .......... ..........

          101                                               150
C. test   CGAACGGGTG AGTAATACAT CGGAACGTGC CTAGTAGTGG GGGATAACTA
Brachym   CGAACGGGTG AGTAATGTAT CGGAACGTGC CCAGTAGTGG GGGATAACTA
A-1       CGAACGGGTG AGTAATACAT CGGAACGTGC CTGGTAGTGG GGGATAACTA
Stripa    .......... .......... .......... .......... ..........
```

Fig. 2A.

```
          151                                                  200
C. test   CTCGAAAGAG TAGCTAATAC CGCATGAGAT CTACGGATGA AAGCAGGGGA
Brachym   CTCGAAAGAG TGGCTAATAC CGCATGAGAA CTGAGGTTGA AAGCGGGGGA
A-1       CTCGAAAGAG TAGCTAATAC CGCATGAGAT CTACGGATGA AAGCGGGGGA
Stripa    .......... .......... .......... .......... ..........

          201                                                  250
C. test   CCTTCGGGCC TTGTGCTACT AGAGCGGCTG ATGGCAGATT AGGTAGTTGG
Brachym   CCTTTGGGCC TCGCGCTACT GGAGCGGCCG ATATCAGATT AGGTAGTTGG
A-1       TCGCAAGACC TCGCGCTACC AGAGCGGCTG GTGGCAGATT AGGTAGTTGG
Stripa    .......... .......... .......... .......... ..........

          251                                                  300
C. test   TGGGGTAAAG GCTTACCAAG CCTGCGATCT GTAGCTGGTC TGAGAGGACG
Brachym   TGGGGTAAAG GCCTACCAAG CCGACGATCT GTAGCTGGTC TGAGAGGACG
A-1       TGGGATAAAA GCTTACCAAG CCGACGATCT GTAGCTGGTC TGAGAGGACG
Stripa    .......... .......... .......... .......... ..........
```

Fig. 2B.

```
          301                                                350
C. test   ACCAG.CCAC ACTGGGACTG AGACACGGCC CAGACTCCTA CGGGAGGCAG
Brachym   ACCAG.CCAC ACTGGGACTG AGACACGGCC CAGACTCCTA CGGGAGGCAG
A-1       ACCAGCCCAC ACTGGGACTG AGACWCGGCC CAGACTCCTA CGGGAGGCAG
Stripa    .......... .......... .......... .......... ..........

          351                                                400
C. test   CAGTGGGGAA TTTTGGACAA TGGGCGAAAG CCTGATCCAG CAATGCCGCG
Brachym   CAGTGGGGAA TTTTGGACAA TGGACGCAAG TCTGATCCAG CAATGCCGCG
A-1       CAGTGGGGAA TTTTGGACAA TGGGCGCAAG CCTGATCCAG CAATGCCGCG
Stripa    .......... .......... .......... .......... ..........

          401                                                450
C. test   T.GCAGGATG AAGGCCCTCG GGTTGTAAAC TGCTTTTGTA CGGAACGAAA
Brachym   T.GCAGGACG AAGGCCTTCG GGTTGTAAAC TGCTTTTGTA CAGAACGAAA
A-1       TNGCAGGATG AAGGCCTTCG GGTTGTAAAC TGCTTTTGTA CGGAACGAAA
Stripa    .......... .......... .......... .......... ..........
```

Fig. 2C.

| | | | | | |
|---|---|---|---|---|---|
| | 451 | | | | 500 |
| C. test | AGCCTGGGGC | TAATATCCCC | GGGTCATGAC | GGTACCGTAA | GAATAAGCAC |
| Brachym | AGGCTCTGGT | TAATACCTGG | GGCTCATGAC | GGTACTGTAA | GAATAAGCAC |
| A-1 | AGGCTCTCTC | TAATACAGAG | AGCCGATGAC | GGTACCGTAA | GAATAAGCAC |
| Stripa | .......... | .......... | .......... | .......... | .......... |
| | 501 | | | | 550 |
| C. test | CGGCTAACTA | CGTGCCAGCA | GCCGCGGTAA | TACGTAGGGT | GCAAGCGTTA |
| Brachym | CGGCTAACTA | CGTGCCAGCA | GCCGCGGTAA | TACGTAGGGT | GCGAGCGTTA |
| A-1 | CGGCTAACTA | CGTGCCAGCA | GCCGCGGTAA | TACGTAGGGT | GCAAGCGTTA |
| Stripa | .......... | .......... | ...GCGGTAA | TACGTAGGGT | GCAAGCGTTA |
| | 551 | | | | 600 |
| C. test | ATCGGAATTA | CTGGGCGTAA | AGCGTGCGCA | GGCGGTTTTG | TAAGACAGTG |
| Brachym | ATCGGAATTA | CTGGGCGTAA | AGCGTGCGCA | GGCGGTTTTG | TAAGACCGAT |
| A-1 | ATCGGAATTA | CTGGGCGTAA | AGCGTGCGCA | GGCGGTCTTG | TAAGACAGAG |
| Stripa | ATCGGAATTA | CTGGGCGTAA | AGCGTGCGCA | GGCGGTGATG | TAAGACAGGC |

Fig. 2D.

| | | | | | |
|---|---|---|---|---|---|
| | 601 | | | | 650 |
| C. test | GTGAAATCCC | CGGGCTCAAC | CTGGGAACTG | CCATTGTGAC | TGCAAGGCTA |
| Brachym | GTGAAATCCC | CGGGCTCAAC | CTGGGAACTG | CATTGGTGAC | TGCAAGGCTG |
| A-1 | GTGAAATCCC | CGGGCTCAAC | CTGGGAACGG | CCTTTGTGAC | TGCAAGGCTG |
| Stripa | GTGAAATCCC | CGGGCTCAAC | CTGGGAATTG | CGCTTGTGAC | TGCATCGCTG |
| | 651 | | | | 700 |
| C. test | GAGTGCGGCA | GAGGGGGATG | GAATTCCGCG | TGTAGCAGTG | AAATGCGTAG |
| Brachym | GAGTGCGGCA | GAGGGGGATG | GAATTCCGCG | TGTAGCAGTG | AAATGCGTAG |
| A-1 | GAGTGCGGCA | GAGGGGGATG | GAATTCCGCG | TGTAGCAGTG | AAATGCGTAG |
| Stripa | GAGTGCGGCA | GAGGGGGATG | GAATTCCGCG | TGTAGCAGTG | AAATGCGTAG |
| | 701 | | | | 750 |
| C. test | ATATGCGGAG | GAACACCGAT | GGCGAAGGCA | ATCCCCTGGG | CCTGCACTGA |
| Brachym | ATATGCGGAG | GAACACCGAT | GGCGAAGGCA | ATCCCCTGGG | CCTGCACTGA |
| A-1 | ATATGCGGAG | GAACACCGAT | GGCGAAGGCA | ATCCCCTGGG | CCTGCACTGA |
| Stripa | ATATGCGGAG | GAACACCGAT | GGCGAAGGCA | ATCCCCTGGG | CCTGCACTGA |

Fig. 2E.

```
          751                                                  800
C. test   CGCTCATGCA CGAAAGCGTG GGGAGCAAAC AGGATTAGAT ACCCTGGTAG
Brachym   CGCTCATGCA CGAAAGCGTG GGGAGCAAAC AGGATTAGAT ACCCTGGTAG
A-1       CGCTCATGCA CGAAAGCGTG GGGAGCACAC AGGATTAGAT ACCCTGGTAG
Stripa    CGCTCATGCA CGAAAGCGTG GGGAGCAAAC AGGATTAGAT ACCCTGGTAG

          801                                                  850
C. test   TCCACGCCCT AAACGATGTC AACTGGTTGT T.GGGTCT.T AACTGACTCA
Brachym   TCCACGCCCT AAACGATGTC AACTGGTTGT T.GGGTAT.T TGCTTACTCA
A-1       TCCACGCCCT AAACGATGTC ANCTGGTTGT T.GGGTCT.T CACTGACTCA
Stripa    TCCACGCCCT AAACGATGTC AACTGGTTGT TTGGGTCTCT TTCTGACTCA

          851                                                  900
C. test   GTAACGAAGC TAACGCGTGA AGTTGACCGC CTGGGGAGTA CGGCCGCAAG
Brachym   GTAACGAAGC TAACGCGTGA AGTTGACCGC CTGGGGAGTA CGGCCGCAAG
A-1       GTAACGAAGC TAACGCGTGA AGTTGACCGC CTGGGGAGTA CGGCCGCAAG
Stripa    GTAACG.AGC TAACGCGTGA AGTTGACCGC CTGGGGAGTA CGGCCGCAAG
```

Fig. 2F.

| | | | | | |
|---|---|---|---|---|---|
| | 901 | | | | 950 |
| C. test | GTTGAAACTC | AAAGGAATTG | ACGGGGACCC | GCACAAGCGG | TGGATGATGT |
| Brachym | GTTGAAACTC | AAAGGAATTG | ACGGGGACCC | GCACAAGCGG | TGGATGATGT |
| A-1 | GTTGAAACTC | AAAGGAATTG | ACGGGGACCC | GCACAAGCGG | TGGATGATGT |
| Stripa | GTTGAAACTC | AAAGGAATTG | ACGGGGACCC | GCACAAGCGG | TGGATGATGT |
| | 951 | | | | 1000 |
| C. test | GGTTTAATTC | GATGCAACGC | GAAAAACCTT | ACCCACCTTT | GACATGGCAG |
| Brachym | GGTTTAATTC | GATGCAACGC | GAAAAACCTT | ACCCACCTTT | GACATGGCAG |
| A-1 | GGTTTAATTC | GATGCAACGC | GAAAAACCTT | ACCCACCTTT | GACATGGCAG |
| Stripa | GGTTTAATTC | GATGCAACGC | GAAAAACCTT | ACCCACCTTT | GACATGTACG |
| | 1001 | | | | 1050 |
| C. test | GAACTTACCA | GAGATGGTTT | GGTGCTCGAA | AGAGAACCTG | CACACAGGTG |
| Brachym | GAATTCCGAA | GAGATTTGGA | AGTGCTCGTA | AGAGAACCTG | CACACAGGTG |
| A-1 | GAATCCTTTA | GAGATAGAGG | AGTGCTCGAA | AGAGAACCTG | CACACAGGTG |
| Stripa | GAATTTGCCA | GAGATGGCTT | AGTGCTCGAA | AGAGAGCCGT | AACACAGGTG |

Fig. 2C.

```
          1051                                                    1100
C. test   CTGCATGGCT GTCGTCAGCT CGTGTCGTGA GATGTTGGGT TAAGTCCCGC
Brachym   CTGCATGGCT GTCGTCAGCT CGTGTCGTGA GATGTTGGGT TAAGTCCCGC
A-1       CTGCATGGCT GTCGTCAGCT CGTGTCGTGA GATGTTGGGT TAAGTCCCGC
Stripa    CTGCATGGCT GTCGTCAGCT CGTGTCGTGA GATGTTGGGT TAAGTCCCGC

          1101                                                    1150
C. test   AACGAGCGCA ACCCTTGCCA TTAGTTGCTA CATTCAGTTG AGCACTCTAA
Brachym   AACGAGCGCA ACCCTTGCCA TTAGTTGCTA ....CGAAAG GGCACTCTAA
A-1       AACGAGCGCA ACCCTTGCCA TTAGTTGCTA ....CGAAAG GGCACTCTAA
Stripa    AACGAGCGCA ACCCTTGTCA TTAGTTGCTA CATTCAGTTG GGCACTCTAA

          1151                                                    1200
C. test   TGGGACTGCC GGTGACAAAC CGGAGGAAGG TGGGGATGAC GTCAAGTCCT
Brachym   TGGGACTGCC GGTGACAAAC CGGAGGAAGG TGGGGATGAC GTCAAGTCCT
A-1       TGGGACTGCC GGTGACAAAC CGGAGGAAGG TGGGGATGAC GTCAAGTCCT
Stripa    TGAGACTGCC GGTGACAAGC CGGAGGAAGG TGGGGATGAC GTCAAGTCCT
```

Fig. 2H.

```
         1201                                               1250
C. test  CATGGCCCTT ATAGGTGGGG CTACACACGT CATACAATGG CTGGTACAAA
Brachym  CATGGCCCTT ATAGGTGGGG CTACACACGT CATACAATGG CCGGTACAAA
A-1      CATGGCCCTT ATAGGTGGGG CTACACACGT CATACAATGG CTGGTACAAA
Stripa   CATGGCCCTT ATAGGTGGGG CTACACACGT CATACAATGG CCGGTACAAA

         1251                                               1300
C. test  GGGTTGCCAA CCCGCGAGGG GGAGCTAATC CCATAAAGCC AGTCGTAGTC
Brachym  GGGTAGCCAA CCCGCGAGGG GGAGCCAATC CCATAAAGCC GGTCGTAGTC
A-1      GGGTTGCCAA CCCGCGAGGG GGAGCCAATC CCATAAAGCC AGTCGTAGTC
Stripa   GGGTCGCAAA CCCGCGAGGG GGAGCCAATC CATCAAAGCC GGTCGTAGTC

         1301                                               1350
C. test  CGGATCGCAG TCTGCAACTC GACTGCGTGA AGTCGGAATC GCTAGTAATC
Brachym  CGGATCGCAG TCTGCAACTC GACTGCGTGA AGTCGGAATC GCTAGTAATC
A-1      CGGATCGCAG TCTGCAACTC GACTGCGTGA AGTCGGAATC GCTAGTAATC
Stripa   CGGATCGCAG TCTGCAACTC GACTGCGTGA AGTCGGAATC GCTAGTAATC
```

Fig. 21.

```
          1351                                                 1400
C. test   GTGGATCAGA ATGTCACGGT GAATACGTTC CCGGGTCTTG TACACACCGC
Brachym   GTGGATCAGC ATGTCACGGT GAATACGTTC CCGGGTCTTG TACACACCGC
A-1       GTGGATCAGA ATGTCACGGT GAATACGTTC CCGGGTCTTG TACACACCGC
Stripa    GTGGATCAGC ATGTCACGGT GAATACGTTC CCGGGTCTTG TACACACCGC

          1401                                                 1450
C. test   CCGTCACACC ATGGGAGCGG GTCTCGCCAG AAGTAGGTAG CCTAACCGTA
Brachym   CCGTCACACC ATGGGAGCGG GTTCTGCCAG AAGTGGTTAG CCTAACCGTA
A-1       CCGTCACACC ATGGGAGCGG GTCTCGCCAG AAGTAGGTAG CCTAACCGCA
Stripa    .......... .......... .......... .......... ..........

          1451                                                 1500
C. test   AGGAGGGCGC TTACCACGGC GGGGTTCGTG ACTGGGGTGA AGTCGTAACA
Brachym   AGGAGGGCGA TCACCACGGC AGGGTTCGTG ACTGGGGTG. ..........
A-1       AGGAGGGCGC TTACCACGGC GGGGTTCGTG ACTGGGGTGA ..........
Stripa    .......... .......... .......... .......... ..........
```

Fig. 2J.

```
          1501                                          1542
C. test   AGGTAGCCGT ATCGGAAGGT GCGGCTGGAT CACCTCCTTT CT
Brachym   .......... .......... .......... .......... ..
A-1       .......... .......... .......... .......... ..
Stripa    .......... .......... .......... .......... ..
```

Fig. 2K.

```
           1                                                  50
C. test    TACGGAACGA AAAGCCTGGG GCTAATATCC CCGGGTCATG ACGGTACCGT
Stripa     .......... .......... .......... .......... ..........
A-1        TACGGAACGA AAAGGCTCTC TCTAATACAG AGAGCCGATG ACGGTACCGT
Brachym    TACAGAACGA AAAGGCTCTG GTTAATACCT GGGGCTCATG ACGGTACTGT
C. terrig  TACGGAACGA AAAGCTTCGG GTTAATACCC TGGAGTCATG ACGGNACCGT
C. acido   TACGGAACGA AAANGCTTCT CCTAATACGA GAGGCCCATG ACGGCACCGT

           51                                                100
C. test    AAGAATAAGC ACCGGCTAAC TACGTGCCAG CAGCCGCGGT AATACGTAGG
Stripa     .......... .......... .......... .....GCGGT AATACGTAGG
A-1        AAGAATAAGC ACCGGCTAAC TACGTGCCAG CAGCCGCGGT AATACGTAGG
Brachym    AAGAATAAGC ACCGGCTAAC TACGTGCCAG CAGCCGCGGT AATACGTAGG
C. terrig  AAGAATAAGC ACCGTNTAAC TACGTGCCAG CAGCCGCGGT AATACGTAGG
C. acido   AAGAATAAGC ACCGTATANC TACGTGCCAG CAGCCGCGGT AATACGTAGG
```

Fig. 3A.

```
          101                                              150
C. test   GTGCAAGCGT TAATCGGAAT TACTGGGCGT AAAGCGTGCG CAGGCGGTTT
Stripa    GTGCAAGCGT TAATCGGAAT TACTGGGCGT AAAGCGTGCG CAGGCGGTGA
A-1       GTGCAAGCGT TAATCGGAAT TACTGGGCGT AAAGCGTGCG CAGGCGGTCT
Brachym   GTGCGAGCGT TAATCGGAAT TACTGGGCGT AAAGCGTGCG CAGGCGGTTT
C. terrig GTNCAAGCGT TANTCGGNAT TACTGGGCGT AAAGCGTGCG CAGGCGGTCT
C. acido  GTGCGAGCGT TACTCGGTAT TACTGGGCGT AAAGCGTGCG CAGGCGGTTA

          151                                              200
C. test   TGTAAGACAG TGGTGAAATC CCCGGGCTCA ACCTGGGAAC TGCCATTGTG
Stripa    TGTAAGACAG GCGTGAAATC CCCGGGCTCA ACCTGGGAAT TGCGCTTGTG
A-1       TGTAAGACAG AGGTGAAATC CCCGGGCTCA ACCTGGGAAC GGCCTTTGTG
Brachym   TGTAAGACCG ATGTGAAATC CCCGGGCTCA ACCTGGGAAC TGCATTGGTG
C. terrig TGTAAGACAG AGGTGANNTC CCCGGNCTCA NCCTGGGAAC TGCCTNTGTG
C. acido  TGTAAGACAG ATGTGACCTC CCCGGTCTCA NCCTGGGAAC TGCATGTGTG
```

Fig. 3B.

```
            201                                                  250
C. test     ACTGCAAGGC TAGAGTGCGG CAGAGGGGGA TGGAATTCCG CGTGTAGCAG
Stripa      ACTGCATCGC TGGAGTGCGG CAGAGGGGGA TGGAATTCCG CGTGTAGCAG
A-1         ACTGCAAGGC TGGAGTGCGG CAGAGGGGGA TGGAATTCCG CGTGTAGCAG
Brachym     ACTGCAAGGC TGGAGTGCGG CAGAGGGGGA TGGAATTCCG CGTGTAGCAG
C. terrig   ACTACAAGGC TGGAGTGCGG NAGAGGGGGA TCGANTTCCG CGTGTAGCAG
C. acido    ACTGCATGGC TAGAGTACGG GAGAGGGGGA TCGAATTCCG CGTGTAGCAG

            251                                                  300
C. test     TGAAATGCGT AGATATGCGG AGGAACACCG ATGGCGAAGG CAATCCCCTG
Stripa      TGAAATGCGT AGATATGCGG AGGAACACCG ATGGCGAAGG CAATCCCCTG
A-1         TGAAATGCGT AGATATGCGG AGGAACACCG ATGGCGAAGG CAATCCCCTG
Brachym     TGAAATGCGT AGATATGCGG AGGAACACCG ATGGCGAAGG CAATCCCCTG
C. terrig   TGANATGCGT NGATATGCGG AGGAACACCG ATGGCGAAGG CACTCCCCTG
C. acido    TGATATGCGT AGATATGCGG AGGAACACCG ATGGCGAAGG CACTCCCCTG
```

Fig. 3C.

| | 301 | | | | 348 |
|---|---|---|---|---|---|
| C. test | GGCCTGCACT | GACGCTCATG | CACGAAAGCG | TGGGGAGCAA | ACAGGATT |
| Stripa | GGCCTGCACT | GACGCTCATG | CACGAAAGCG | TGGGGAGCAA | ACAGGATT |
| A-1 | GGCCTGCACT | GACGCTCATG | CACGAAAGCG | TGGGGAGCAC | ACAGGATT |
| Brachym | GGCCTGCACT | GACGCTCATG | CACGAAAGCG | TGGGGAGCAA | ACAGGATT |
| C. terrig | GGCCTGCACT | GACGCTCATA | CACGAANGCG | TGGGGAGCAA | ACAGTATT |
| C. acido | GCCCTGTTCT | GACGCTCATA | CACGAAAGCG | TGGGGAGCAA | ACAGTATT |

Fig. 3D.

# DEGRADATION OF ENVIRONMENTAL TOXINS BY A FILAMENTOUS BACTERIUM

This application is a continuation-in-part application based on application Ser. No. 08/599,867, filed Feb. 12, 1996, now abandoned, which is a continuation of application Ser. No. 08/246,865, filed May 20, 1994, now abandoned, and which is hereby incorporated by reference into the present application.

This invention was made with government support under National Institute of Environmental Health Services Grant No. NIEHS ES 04696. The government has certain rights in the invention.

FIELD OF THE INVENTION

This invention relates to the biological degradation of halide-containing substances present in the environment such as trichloroethylene (TCE) and dichloroethylene (DCE) using a newly discovered filamentous bacterium.

BACKGROUND OF THE INVENTION

Environments contaminated with the chlorinated solvents trichloroethylene (TCE) and dichloroethylene (DCE) are major cleanup problems, and will involve hundreds of millions in Superfund expenditures in the coming years. TCE is a common ground-water contaminant in the United States as a result of solvent spills and dry-cleaning chemical disposal. Cis-1,2-dichloroethylene (DCE) is also a common ground-water contaminant that originates from anaerobic dehalogenation of TCE in the environment. These compounds are potential carcinogens and cannot be removed effectively from ground water using conventional water purification processes. For many sites, bioremediation is the only practical approach for cleanup, but the use of previously known solvent-metabolizing microorganisms has often been hindered by their extreme sensitivity to the toxic effects of intermediates produced as the result of these bacteria's degradation of TCE and related compounds, and by their sensitivity to high concentrations of TCE itself.

Various types of bacteria have been shown to degrade TCE, including methanotrophs, toluene-degraders, phenol-degraders, propane oxidizers, and nitrifiers. (Fogel et al., 1986; Wackett et al., 1989; Ensley et al., 1991). These bacteria degrade TCE by a process of "cometabolic degradation," in which substrates that support growth induce nonspecific monooxygenase or dioxygenase enzymes that fortuitously can also degrade TCE and other chlorinated aliphatic compounds (CACs). The dioxygenases and monooxygenases both require oxygen and reducing power in the form of NADH.

When methanotrophs, the most extensively studied of this type of bacteria, metabolize trichloroethylene (TCE), dichloroethylene (DCE), or vinyl chloride by means of oxidative cometabolism, the resulting chemical intermediaries are known to be toxic to these microorganisms at relatively low levels (e.g., Alvarez-Cohen and McCarty, 1991a; Alvarez-Cohen and McCarty, 1991b; Alvarez-Cohen and McCarty, 1991c; Rasche et al., 1991; Oldenhuis et al., 1989). Moreover, the presence of methane competitively inhibits TCE degradation by methanotrophs (Strand et al., 1990). Consequently, the use of methanotrophs in bioremediation is severely limited.

Bacteria other than methanotrophs are also known to degrade CACs. For example, Burkholderia (Pseudomonas) cepacia G4 (U.S. Pat. Nos. 4,925,802, and 5,071,755) expresses elevated levels of a CAC-degrading toluene ortho-monooxygenase enzyme in the presence of phenol, toluene, o-cresol, or m-cresol (originally called "Pseudomonas cepacia G4", this bacterium has been reclassified as "Burkholderia cepacia G4," Yabuuchi et al., Microbiol. Immunol. 36:1251–1275, 1981). This bacterium, isolated from an industrial waste site water sample, is strictly aerobic. The G4 isolate is reportedly a gram-negative, rod-shaped bacterium that grows predominantly in pairs and short chains, and can utilize carbohydrates as a carbon source. This organism reportedly consumes TCE at a rate of about 2.5 nmol/minute per mg of protein with a $K_S$ of 3 $\mu$M (Folsom et al., 1990). "Intermediate toxicity," i.e., toxicity resulting from CAC degradation products, was observed in studies of Pseudomonas putida F1, as evidenced by a decrease in growth rate (Wackett and Householder, 1989). This study also reported that TCE damaged the P. putida's intracellular proteins.

In other studies, phenol was utilized in situ to stimulate natural microorganisms to degrade CACs (Hopkins et al., 1993a; Hopkins et al., 1993b). Phenol-degrading microorganisms were readily stimulated, and phenol removal from the injection site was complete after 170 hours. Cometabolic degradation of TCE and DCE was also observed, and phenol-degrading microorganisms were found to remove TCE more effectively than did methanotrophic organisms stimulated by methane addition in concurrent tests. Some laboratory studies with phenol/toluene oxidizers have been done (Folsom et al., 1990; Nelson et al., 1988; Shields et al., 1989; Wackett and Householder, 1989), although such bacteria are less well-studied than the methanotrophs. However, it has been demonstrated that the toluene-degrader Pseudomanas putida F1 suffers toxic cellular effects from TCE degradation byproducts (Wackett and Householder, 1989). Another phenol-degrading bacteria reported to metabolize TCE is Alcaligenes eutrophus JMP134 (Harker and Kim, 1990).

SUMMARY OF THE INVENTION

Provided are substantially purified cultures of a new phenol-oxidizing bacteria that is capable of the cometabolic degradation of TCE and DCE and that is resistant to the toxic effects of metabolic intermediates produced by this degradation (Bielefeldt et al., 1995, which is hereby incorporated by reference). This new bacterium has a filamentous appearance and was first isolated from a surface-water sample grown under nitrogen-limiting conditions and with phenol provided as a carbon source. When used for bioremediation, this novel CAC-degrading microorganism has advantages over many of the previously known organisms that degrade TCE. The invention provides a straight-forward method for obtaining the filamentous bacteria in enrichment cultures inoculated with environmental samples such as groundwater. Moreover, the growth advantage of this new microbe is shown to be so great that under nitrogen-limiting growth conditions it can overcome other microorganisms that have been inoculated into the cultures. The invention further provides a representative strain of the filamentous bacterium that was purified from a mixed culture by using standard microbiological techniques. This strain, called A-1, has been deposited with the American Type Culture Collection in accordance with the Budapest Treaty on May 20, 1994, at the American Type Culture Collection under the accession No. ATCC 55581.

The present invention provides a method of bioremediation that involves contacting an environmental sample contaminated with chlorinated aliphatic compounds with a previously unknown filamentous bacterium capable of metabolizing chlorinated aliphatic compounds. This newly discovered filamentous bacterium can metabolize CACs in the presence or in the absence of phenol, although phenol induces elevated levels of the CAC-degrading enzyme. The filamentous bacteria can be used to decontaminate soil, water, and air samples. Isolates of the subject bacterium can be identified by their unique constellation of morphological and physiological properties. The new bacterium has non-sheathed rod-shaped cells filamentous in appearance and ranging in length from 20–200 μm, is aerobic, gram-negative, and when grown under nitrogen-limiting conditions accumulates poly-β-hydroxybutyrate (PBB) in intracellular granules. Moreover, the bacterium is capable of growing in the presence of 0.2% phenol or 1% saturated toluene vapor, and does not grow on carbohydrates.

The unique phylogenetic status of this novel bacterium has been confirmed by sequencing its 16S rRNA gene and comparing the sequences thus obtained with 16S rRNA sequences from other bacteria. Application of this well-established form of phylogenetic analysis indicated that this bacteria does not correspond to any known species for which 16S rRNA sequences are available. In light of the bacterium's unique morphology, these findings suggest that the filamentous bacterium may represent a new genus or species.

The subject microorganism is more suited for bioremediation than methanotrophic bacteria due to its ability to tolerate metabolic intermediates produced from CACs, its tolerance for relatively high concentrations of substrate, and its having a higher rate of endogenous transformation of CACs. Moreover, it is shown here to tolerate higher TCE concentrations than other phenol-degrading microorganisms have been shown to tolerate. Thus, the subject microorganism can provide bioremediation in both aerobic treatment systems, suspended or fixed growth systems, or in gas biofilters.

BRIEF DESCRIPTION OF THE DRAWINGS

FIGS. 2A–2K show the DNA sequences corresponding to the 16S rRNA genes from several bacteria. The bacteria whose sequences are shown in FIG. 2 are *Comamonas testosteroni* ATCC No. 11996, *Brachymonas denitrificans* AS-P1, strain A-1, and Stripa research mine environmental clone, and these sequences correspond, respectively, to SEQ ID NOS:1–4; and FIGS. 3A–3D show an excerpt of 16S rDNA sequences from the indicated microorganisms. The bacteria whose sequences are shown in FIGS. 3A–3D are *Comamonas testosteroni* ATCC No. 11996, Stripa environmental clone, strain A-1, *Brachymonas denitrificans* AS-P1, *Comamonas terrigena* ATCC No. 8461, and *Comamonas acidovorans* ATCC No. 15668, and these sequences correspond to SEQ ID NOS:5–10, respectively. Only a portion of the 16S rDNA sequence was available for the Stripa environmental clone.

DETAILED DESCRIPTION OF THE PREFERRED EMBODIMENT

Figure 1A:
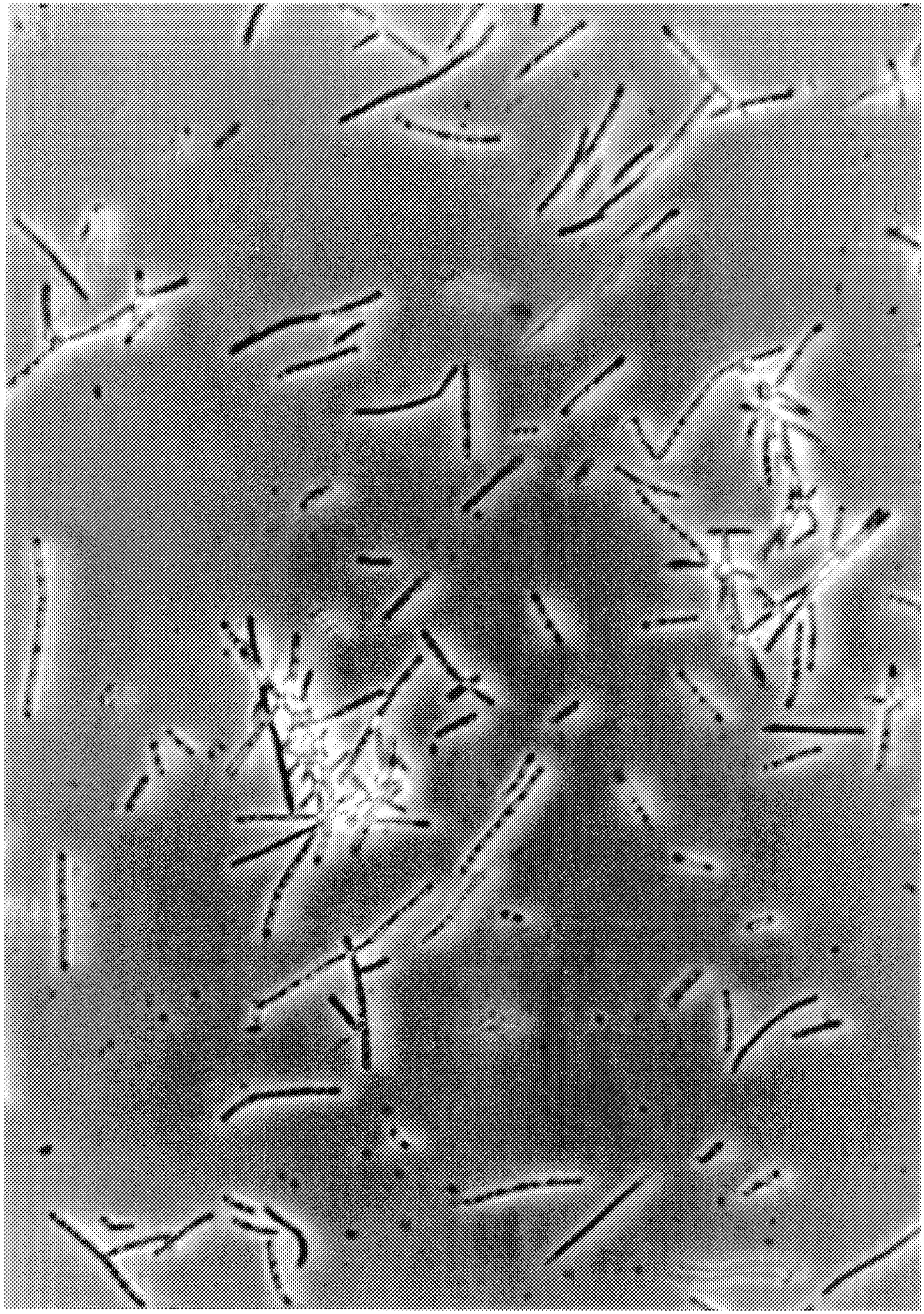
FIGS. 1A and 1B are photomicrographs of the filamentous bacterium.

The subject invention provides methods of bioremediation comprising contacting an environmental sample contaminated with chlorinated aliphatic compounds with a unique bacterium capable of metabolizing chlorinated aliphatic compounds in the environmental sample. The improvement offered by this invention is the provision of substantially purified cultures of a previously unknown bacterium that is useful for bioremediation. This bacterium has non-sheathed rod-shaped cells filamentous in appearance and ranging in length from 20–200 μm. The bacterium is aerobic, gram-negative, accumulates intracellular poly-β-hydroxybutyrate in intracellular granules when grown under nitrogen-limiting conditions, is capable of growing in the presence of 0.2% phenol or 1% saturated toluene vapor, and does not grow on carbohydrates. Methods are provided for isolating substantially pure cultures of this new bacterium from environmental samples as well as methods for confirming that new isolates are substantially identical to the representative strain A-1 whose isolation is described here, and which was deposited in accord with the Budapest Treaty on May 20, 1995, at the American Type Culture Collection at 12301 Parklawn Drive, Rockville, Md. 20852, under the Accession No. 55581. The new bacterium can be used to decontaminate soil, water, or air samples.

In one embodiment of the methods provided by the invention, rather than contacting the contaminated sample directly with the bacterium, samples of soil or water are contacted with a stream of air into which the volatile chlorinated aliphatic compounds are thereby transferred. The contaminant-bearing air then is contacted with the subject bacterium. In other embodiments, contaminated soil or water are brought into direct contact with the bacterium. Alternatively, contaminated sites can be inoculated with the bacterium along with a single dose of phenol.

The subject bacterium differs from previously known bacteria not only in its morphology and physiology, but with respect to sequences present in certain regions of its 16S ribosomal RNA (rRNA). In recent years, 16S rRNA sequence analysis has provided taxonomists with an invaluable tool for determining phylogenetic relationships among bacteria. Overall, the 16S rRNA molecule is highly conserved, but some regions of the molecule are subject to a relatively low degree of evolutionary constraint, hence can sustain numerous base sequence changes without loss of 16S rRNA function (see, e.g., Woese, 1987; Olsen et al., 1986; Gutell et al., 1994; Olsen et al., 1994, all of which are hereby incorporated by reference). These so-called "hypervariable regions" have been sequenced for a wide array of microorganisms, and the number and types of differences within these regions evaluated to determine evolutionary relationships among bacterial genera and species. A more modern approach to phylogenetic analysis of rRNA genes involves a computer-based comparison of the entire 16S rDNA sequence from different organisms, with the variable rates of evolution at each base position being taken into account by the computer program.

Because of the sequence differences among bacteria, the 16S rRNA sequences have been exploited as a means for rapidly confirming whether field isolates of similar-appearing bacteria belong to the same or to different species (Moncla et al., 1990, which is hereby incorporated by reference). These investigators used radioactively-tagged 24-base oligonucleotide probes complementary to the hypervariable regions of the 16S rRNA of *B. gingivalis* to analyze numerous isolates of oral bacteria associated with periodontal disease. Several different probes were hybridized under stringent conditions with filter-immobilized DNA from a large number of bacteria isolated from the mouths of different patients. The hybridization conditions used by Moncla et al. were 0.6M NaCl, 90 mM Tris, pH 8.0, 10 mM EDTA, 30% deionized formamide, 0.5% sodium dodecyl sulfate (SDS), 5×Denhardt solution (Sigma, pH 8.0), 100 μg hydrolyzed carrier RNA per ml of hybridization buffer, with 4 hours or more incubation at 42° C. with gentle shaking, in the presence of about 5 ng of $^{32}P$-labeled oligonucleotide (about 1000–1200 cpm) per ml of hybridization buffer. These conditions ensured that the labeled probe would attach to the filter-bound DNA only if well-matched duplexes (i.e., hybrids) were formed. The filters were washed twice at 55° C. (or at 50° C.) with 0.09M NaCl, 9 mM Tris, 1 mM EDTA, 0.1% SDS, pH 8.0 to remove unbound probes, and the hybridized probes were then detected by autoradiography. Other stringent hybridization conditions are known, i.e., conditions that permit only well-matched complementary nucleotide strands to form duplexes during the incubation period (see Sambrook et al., 1989, which is hereby incorporated by reference). A number of probes tested by Moncla et al. proved to be 100% specific when compared with standard microbiological methods for classifying these same bacteria. Thus, Moncla et al. demonstrated that hybridization under stringent conditions can provide a reliable means for determining whether bacterial isolates belong to the same or to different species. Similarly, probes selected from the 16S rDNA sequences of strain A-1 can be used to confirm the identity of field isolates of the subject filamentous bacterium.

The 16S rDNA of the representative strain A-1 has been sequenced using published methods (Dyksterhouse et al., 1995) and consists of the nucleotide sequences depicted in SEQ ID NO:3. SEQ ID NO:7 presents a subset of the sequences in SEQ ID NO:3. Strain A-1 was obtained by initially streaking a sample of the mixed culture of the filamentous bacteria, then repeatedly streaking and picking individual colonies. The A-1 strain resulting from these isolation procedures has been deposited at the American Type Culture Collection under the accession No. ATCC 55581. The scope of the invention includes microorganisms whose 16S ribosomal DNA is substantially identical to the sequences depicted in SEQ ID NO:3 and that are aerobic, gram-negative, have non-sheathed, filamentous, rod-shaped cells, under nitrogen-limiting conditions accumulate intracellular poly-β-hydroxybutyrate in intracellular granules, that are capable of growing in the presence of 0.2% phenol or 1% saturated toluene vapor, and that do not grow on carbohydrates. For the purposes of this invention, nucleotide sequences "substantially identical" to SEQ ID NO:3 means that the DNA in question will hybridize with DNA from strain A-1 under stringent conditions.

The novel microorganism of the subject invention became dominant when non-sterile culture medium was inoculated with surface water and maintained under aerobic nitrogen-limiting conditions in the presence of phenol, a substance capable of inducing phenol-degrading enzymes that also have the capacity to degrade CACs. "Nitrogen-limiting conditions" means that the culture media contains about 200 g $NH_4Cl$ for every 1000 g phenol used as a carbon source. This is a lower ratio of carbon:nitrogen than is commonly used for cell growth.

In several subsequent experiments, the subject microorganism became predominant in other cultures maintained under nitrogen-limiting conditions in the presence of phenol when the cultures were inoculated from a pure culture of *Burkholderia cepacia* G4. These cultures were not inoculated with the filamentous bacterium.

A pure culture of the filamentous microorganism was obtained by repeatedly streaking the filamentous bacteria from a mixed culture using standard microbiological techniques, but the microorganism was observed to grow somewhat better in nitrogen-limited cultures in which sterility was not maintained. It is possible that the subject microorganism benefits in some way from the presence of small amounts of unidentified microorganisms in non-sterile cultures. Mixed cultures in which one microorganism enhances the growth of another are commonly termed "consortia," and the mixed cultures predominated by the filamentous bacteria are referred to as "consortia." However, in pure culture the subject microorganism grows reasonably well and can still degrade TCE.

For the purposes of this invention, a "substantially-purified culture" of the novel bacterium includes a pure culture obtained by repeated streaking, as well as a non-sterile culture in which the filamentous bacterium predominates. The term "substantially-purified" indicates a culture which, when inspected microscopically at 1000× magnification, appears visually to contain at least 70% by mass of the filamentous bacterium. More typically, mixed cultures of the filamentous bacterium appear visually to contain about 90% by mass of the filamentous bacterium at this level of magnification.

The physical appearance of this new microorganism is strikingly different from any morphological forms reported for the organism's nearest phylogenetic relatives. No CAC degradation work with a microorganism having this appearance has apparently been reported. Cultures enriched for this organism can be maintained for long periods under non-sterile conditions by providing intermittent doses of phenol and an inorganic nutrient solution in which nitrogen is limited. Established cultures can be maintained even under nitrogen-sufficient culture conditions.

The lack of TCE intermediate toxicity effects on the enriched culture of the subject microorganism is a major advantage for its use over methanotrophs in bioremediation. The observed TCE transformation capacity of this new bacteria is substantially greater than values reported for most other cometabolic bacteria that are affected by intermediate toxicity (Bielefeldt et al., 1995). This advantage could be critical in terms of designing a treatment system, as phenol-metabolizing cultures could potentially maintain degradation for a longer period than methanotrophs, with whose use TCE degradation rates decline rather rapidly due to intermediate toxicity. Furthermore, when phenol is present, this new microorganism has been shown to tolerate and degrade concentrations of TCE as high as 130 mg/l, and concentrations of DCE up to 83 mg/l (Bielefeldt et al., 1995). Tolerance to high concentrations of contaminants would be critical for bacteria used to treat fairly concentrated waste streams. Moreover, the bacteria of the subject invention degrades TCE at concentrations higher than those previously reported to be degraded *Burkholderia cepacia* G4 (Bielefeldt et al., 1995).

Besides its unique filamentous appearance, the subject microorganism has a constellation of physiological properties that set it apart from previously-known microorganisms. The new organism is aerobic, gram-negative, has non-sheathed rod-shaped filamentous cells, accumulates intracellular poly-β-hydroxybutyrate in intracellular granules under nitrogen-limiting conditions, can grow in the presence of 0.2% phenol or 1% saturated toluene vapor, and does not grow on carbohydrates. Based on these characteristics, the new bacteria is clearly different and distinct from its known phylogenetic relatives *Comamonas acidovorans* and *Comamonas testosteroni.*

Figure 1B:
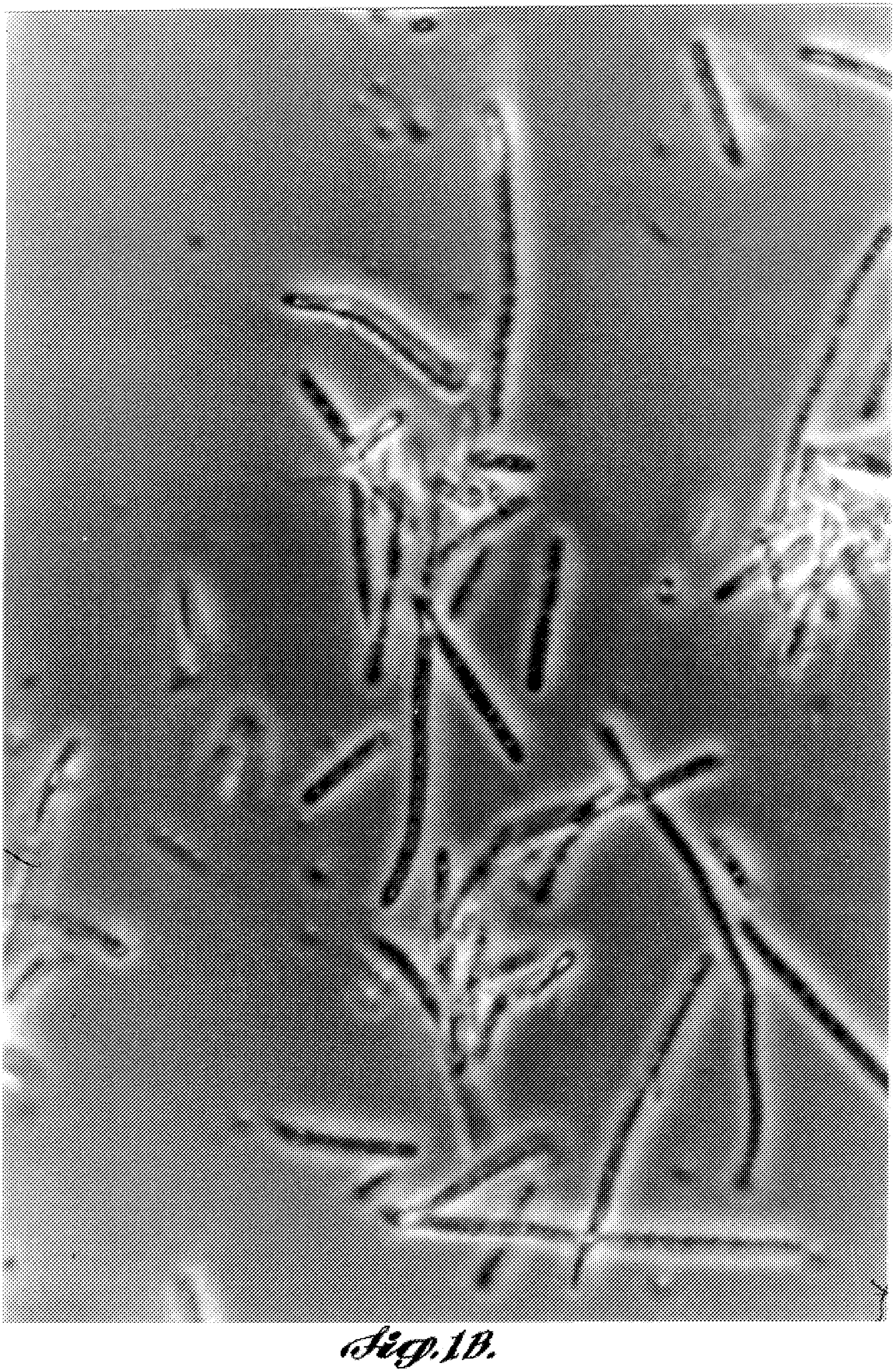

Bacterial isolates of the subject invention can be identified by their unique properties, i.e., their filamentous appearance combined with the constellation of traits listed above, but their identities can be further confirmed by analyzing the nucleotide sequence of their 16S rDNA. Using the A-1 strain as a representative source of the filamentous bacteria's DNA, the entire 16S rRNA gene of this new organism has been sequenced and compared with 16S rDNA sequences from other bacteria (Example 3, FIGS. 1 and 2, and Tables 1 and 2). When the A-1 16S rDNA sequences were compared with three others for which all or most of the 16S rDNA sequence is known, results indicated that the filamentous bacteria's 16S rDNA gene differed from the nearest related bacteria by 4.62% (FIG. 2 and Table 1). A smaller region of A-1 16S rDNA sequence was compared with two additional bacteria for which only a limited region of 16S rDNA sequence was available (FIG. 3 and Table 2). In this latter comparison, which also included the four bacteria from FIG. 2, the A-1 sequences differed from the most closely related bacterium at 4.18% of the nucleotide positions (Table 2). Thus, a 16S rDNA analysis of this type can be applied to field isolates of the subject bacteria either as an alternative to a full determination of physiological properties, or as a means of further confirming an isolate's identity.

The subject bacteria can be used in bioremediation applications in several ways. Treatment of air-stripping vapors is among the preferred applications. For this procedure, water or soil carrying TCE is first aerated, and the volatile TCE is transferred to the air stream with which the contaminated water or soil is aerated. For example, water is pumped out of the ground and aerated at the surface. The TCE-bearing air stream is passed subsequently through a biofilter or bioreactor in which the subject microorganisms are present. The biofilter or bioreactor is inoculated with a pure culture of the subject microorganism, which thereafter will remain the predominant microorganism under nitrogen-limiting conditions without any need to maintain the filter under sterile conditions. Alternatively, the bioreactor can be inoculated with a mixed culture in which the novel filamentous bacterium is the predominant organism.

TABLE 1

| | Strain A-1 | *C. testosteroni* (ATCC 11996) | Stripa research mine derived environmental clone | *Brachymonas denitrificans* AS-P1 |
|---|---|---|---|---|
| Strain A-1 | 1.000 | 0.9538 | 0.9383 | 0.9449 |
| *C. testosteroni* | | 1.000 | 0.9520 | 0.9463 |
| Stripa environmental clone | | | 1.000 | 0.9394 |
| *Brachymonas denitrificans* | | | | 1.000 |

TABLE 2

| | Strain A-1 | *C. testosteroni* (ATCC 11996) | *C. terrigena* (ATCC 8461) | *C. acidovorans* (ATCC 15668) | Stripa research mine derived environmental clone | *Brachymonas denitrificans* AS-P1 |
|---|---|---|---|---|---|---|
| Strain A-1 | 1.000 | 0.9425 | 0.9368 | 0.8908 | 0.9582 | 0.9454 |
| *C. testosteroni* | | 1.000 | 0.9511 | 0.8908 | 0.9620 | 0.9454 |
| *C. terrigena* | | | 1.000 | 0.9253 | 0.9468 | 0.9397 |
| *C. acidovorans* | | | | 1.000 | 0.9049 | 0.8994 |
| Stripa environmental clone | | | | | 1.000 | 0.9544 |
| *Brachymonas denitrificans* | | | | | | 1.000 |

As an alternative to air-stripping, contaminated water can be treated directly with the subject bacteria. As an additional alternative, pure or enriched cultures of the subject bacteria can be injected into contaminated ground sites, in which case the growth of injected microorganisms may be enhanced by co-injection of substances such as phenol or toluene that induce the enzymes responsible for TCE degradation. The continuous presence of phenol is not necessary, as the phenol-induced enhancement of TCE-degradation persists for many hours after the phenol has been entirely degraded (see Example 5). The subject bacteria also have been found to be particularly effective in degrading benzene, toluene, ethylbenzene, and xylenes, substances common in gasoline spills, hence could be used for clean-up of such spills.

The invention is further described in the following examples.

EXAMPLES

Example 1

Isolation of Filamentous Bacteria Capable of Metabolizing Chlorinated Aliphatic Compounds Enrichment cultures of phenol-degrading bacteria were grown in mixed, flow-through reactors, and biomass from these reactors harvested for use in batch-fed, serum bottle tests to study the degradation of phenol and chlorinated aliphatic compounds. The cultures were grown at 20° C. in continuously stirred 4L flasks stoppered with sterilized glass wool. However, the enrichment cultures were not intended to be sterile cultures, but rather were designed to encourage or select for the outgrowth of naturally-occurring bacteria that tended to thrive and become predominant under the provided growth conditions.

(1) NL3

A 4L flask was inoculated with water from a stream running through an old capped landfill in a parking lot located in Seattle, Wash. The pH was maintained at about 7.0 by adding sodium bicarbonate. The reactor feed solution contained 1000 mg/l phenol, 700 mg/l $KH_2PO_4$, 1000 mg/l $K_2HPO_4$, 200 mg/l $NH_4Cl$, 50 mg/l $CaCl_2$, 30 mg/l $MgSO_4$, 10 mg/l NaCl 0.055 mg/l $CuCl_2$ $H_2O$, 0.148 mg/l $ZnCl_2$, 0.022 mg/l $NiCl_2$ $6H_20$, 0.880 mg/l $FeSO_4$ $7H_2O$, 0.135 mg/l $Al_2(SO_4)_3$ $18_2O$, 0.282 mg/l $MnCl_2$ $4H_2O$, 0.056 mg/l $CoCl_2$ $6H_2O$, 0.032 mg/l $Na_2MoO_4$ $2H_2O$, 0.049 mg/l $H_3BO_3$. The initial nutrient solution in the flask was the same as the feed solution except for the phenol.

In the culture flask (or "bioreactor"), the chemical oxygen demand (COD) to N ratio in the feed (from phenol and $NH_4Cl$, respectively) was 100:2.2 gCOD/g N. "Chemical oxygen demand" is a measure of the concentration of metabolizable carbon present in the culture. The concentration of phenol in the flask was maintained at about 0.5 mg/l, and phenol was the sole carbon source provided. A timer was used to intermittently feed the reactor at approximately 0.6 ml/min at an average phenol loading rate of 0.36 g/g volatile suspended solids per day (VSS-d) and to withdraw reactor liquid every 6 hours at a rate of about 7 ml/min for 12 minutes. The reactor liquid volume varied from 2–2.7 L and the concentration of VSS varied, but ranged from about 400–600 mg/L. Several weeks after the pH of this culture was temporarily dropped to 4.0 and the phenol concentration raised to 1 mg/L, a large filamentous bacterium was observed to dominate this culture. It is not known whether this temporary change in culture conditions affected the subsequent outgrowth of the subject bacteria.

(2) Nitrogen-Limited (NL1)

After the NL3 culture had been established, a separate non-sterile culture, designed NL1, was inoculated from a slant of *Burkholderia cepacia* strain G4, and fed with the above-described feed solution for 50 minutes every two hours at an overall loading of about 0.18 g phenol/L culture volume per day. Nitrogen-limiting conditions were maintained as described above. Effluent from the reactor was pumped out every six hours at a rate of about 7 ml/min for 12 minutes, and fresh medium pumped in at a similar rate. Instead of producing a culture predominated by *B. cepacia* G4 as expected, within three weeks the growth reactor became predominated by a filamentous bacteria that was morphologically very different from G4 and that was identical in appearance to the filamentous bacteria of NL3. The filamentous bacteria's outgrowth and predominance in NL1 apparently was a response to its selective advantage under the provided growth conditions.

(3) NL2

Inoculated from a *B. cepacia* G4 slant, this culture was fed with the feed solution described above for 2 min of every 5 min at an overall loading of about 0.18 g phenol/L-d; the feed COD:N ratio was about 45:1 gCOD/g N. This culture, like NL1, was intended to give rise to a mixed culture predominated by *B. cepacia* G4, but instead, became predominated within three weeks by a filamentous bacteria identical in appearance to that observed in NL3 and NL1. Under these growth conditions, the filamentous bacteria apparently has a reproducible growth advantage over *B. cepacia* G4 and other microorganisms that may have been present in the non-sterile bioreactor.

(4) NNL

To test the capacity of the filamentous bacteria to tolerate increased nitrogen, after NL2 was maintained for three months under conditions described above, the COD:N ratio in the feed was changed to 100:5.6 by raising the $NH_4Cl$ concentration to 300 mg/l and adding $NaNO_3$ at 300 mg/l. This culture was thereafter designated "NNL," or "non-nitrogen limited." Despite the increase in nitrogen concentration, the predominant filamentous bacteria initially present in this culture did not become displaced by other microorganisms. Thus, the filamentous bacteria does not absolutely require nitrogen-limiting conditions in order to remain the dominant organism in a culture. However, observations indicated that the organism grows somewhat better under nitrogen-limiting conditions.

(5) Isolation of Strain A-1

The large filamentous bacteria were further purified by streaking onto 1.5% agar medium containing 500 mg/l $KNO_3$, 200 mg/l $MgSO_4$, 15 mg/l $CaSO_4$, 63 mg/l $(NH_4)_2SO_4$, 425 mg/l $Na_2HPO_4$, 200 mg/l $KH_2PO_4$, 1 mg/l $FeSO_4$ $H_2O$, 0.5 mg/l NaEDTA, 0.1 mg/l $CuSO_4$, 0.1 mg/l $ZnSO_4.7H_2O$, 0.03 mg/l $NaMoO_4.2H_2O$, 0.02 mg/l $MnSO_4.2H_2O$, 0.02 mg/l $H_3BO_3$, 0.02 mg/l $NiSO_4.6H_2O$, 0.01 mg/l $CoSO_4.7H_2O$, 50 or 100 mg/l phenol. Phenol was the sole source of carbon and energy, and there was no significant growth if phenol was omitted from the medium. Colonies appeared within 2 days. Individual colonies were picked and streaked several times to obtain a colony that presumably originated from a single bacterial cell. The purified culture that arose from this colony was named strain A-1 (ATCC No. 55581).

Example 2

Characteristics of the Filamentous Phenol-Degrading Bacteria

The predominant bacteria in NL3, NL1, NL2, NNL (described in Example 1), and strain A-1 were virtually indistinguishable from one another when examined under the microscope, although bacteria from the NNL culture had somewhat shorter filaments and fewer intracellular deposits. The filamentous bacteria exhibited long filaments ranging in length from 20–200 $\mu$m, contained large bluish intracellular deposits, and were capable of degrading TCE and utilizing phenol as their sole carbon source. Within the filaments, neither flagella nor septa were directly observed. The morphology of the subject bacteria was clearly very different from the much shorter inclusion-free rods of the phenol-degrader *B. cepacia* G4.

The filamentous bacteria's capacity to degrade phenol was determined in sterile 160 ml serum bottles containing 10–70 ml of fresh nutrient medium brought up to a total of 80 ml from the enrichment cultures. The nutrient medium was the same as used for the growth reactor feed but without the phenol. The medium was pre-aerated with oxygen for 15–30 minutes before use. Phenol (10–40 mg/L) was spiked into bottles containing aliquots of the mixed cultures. After an appropriate interval to permit phenol degradation, the concentration was measured by removing 1 g of sample to a 4 ml vial containing 4-chlorophenol as an internal standard, then adding 40 =l each of $K_2CO_3$ and acetic anhydride. After 30 min at room temperature to permit acetylation of non-degraded phenol, 1 ml of hexane was added and the sample vortexed for 2 min. After centrifugation to separate the layers, the hexane layer was collected and phenol measured by gas chromatography using standard procedures (Bielefeldt et al., 1995). Alternatively, phenol was measured colorimetrically by adjusting a culture sample to pH 7.9, then reacting with 4-aminoantipyrene and potassium ferricyanide to produce a yellow-to-red product. After 15 min, samples were analyzed spectrophotometrically at 500 nm. Concentrations of phenol were determined colorimetrically by comparison to standards containing known amounts of phenol.

Samples of NL1, NL2, NL3, and NNL all were shown to be capable of degrading phenol. Extensive testing focused on NL1, NL2, and NNL. For those three cultures, degradation of phenol in batch tests was essentially linear, following zero-order kinetics down to less than 0.5 mg/L. For one experiment with samples from NL1, the phenol concentrations tested were 5, 8, 16, and 26 mg/l. All the degradation curves were linear, and the rates observed for the highest and the lowest concentrations were very similar, consistent with zero-order kinetics. Overall, the rates of phenol degradation ranged from 2.2–16.4 g phenol/g-d. In general, rates were higher when the culture was grown under nitrogen-sufficient conditions rather than nitrogen-limiting conditions. In most batch test cultures, phenol degradation was complete in less than 1 h, and often in less than 15 min. Moreover, when high concentrations of TCE were added, a decrease in the rate of phenol degradation was observed.

These results were compared with published data describing phenol degradation by *Burkholderia* (*Pseudomonas*) *cepacia* G4 (Folsom et al., 1990). This publication indicated that for G4, phenol degradation rates varied with phenol concentration, with increasing rates up to about 5 mg/l, and then decreasing rates due to substrate toxicity. Moreover, Folsom et al. observed that TCE significantly inhibited phenol degradation by G4.

Example 3

Characterization of Strain A-1

The representative strain A-1 is capable of growing on low concentrations of phenol and toluene, and does not grow when carbohydrates form the sole carbon source. While the filamentous bacterium occasionally appeared to be motile when grown in mixed cultures, strain A-1 is non-motile. A whole cell fatty acid composition of strain A-1 was performed using the MIDI gas chromatographic bacterial identification system. Based on the results, the closest match in the TSBA database was *Comamonas* (Pseudomonas) *acidovorans.* (The "TSBA database" is a commercially available database from MIDI in which identification of unknown bacterial strains is based on comparing the whole cell fatty acid composition of unknown strains to strains that are present in the MIDI database. Cultures to be identified must be grown under incubation conditions that are specified by MIDI). However, A-1 exhibited phenotypic properties quite different from previously described type strains of Comamonas, which are motile and have notably shorter rods.

To perform phylogenetic analysis, the 16S rDNA of A-1 was amplified using primers specific for 16S rRNA genes, and the amplification products cloned and sequenced as described (Dyksterhouse et al., 1995). Sequencing was performed in both directions using the ABI automated sequencer and the Cycle-Sequencing kit. A computer program (fastDNAml) was used to compare the resulting sequences with other known 16S rDNA sequences and to create a phylogenetic tree using the maximum likelihood method. Results indicated that A-1 is a member of the β subdivision of the Proteobacteria, but is not closely related to *B. cepacia,* or other Burkholderia species.

The Ribosomal Database Project files indicated that A-1's closest relative based on 16S rDNA sequence is *Comamonas testosteroni* (the strain of *C. testosteroni* with which the A-1 sequence was compared was described in U.S. Pat. No. 5,120,652), a species closely related to *Comamonas acidovorans,* which MIDI analysis identified as the filamentous bacteria's closest relative. However, *C. testosteroni* and the filamentous bacterium differ significantly. *C testosteroni* can grow on carbohydrates while A-1 cannot. Moreover, *C. testosteroni* exhibits gram-negative rods that are 0.5–0.7 $\mu$m wide and 1.5–3.0 $\mu$m long (U.S. Pat. No. 5,120,652), in contrast to the long filaments (20–200 $\mu$m) of the present isolate. The data in Table 1 suggests that A-1 may be a new species of Comamonas or may belong to a previously unknown genus.

A computer-based comparison was performed of A-1 16S rDNA sequences to 16S rDNA from other bacteria as described in Dyksterhouse et al. (1995). Results for the most closely-related bacteria for which sequences were available are illustrated in Tables 1 and 2 and in FIGS. 2 and 3. These microorganisms, the closest known phylogenetic relatives to strain A-1, all belong to the β-Proteobacteria. FIG. 2 shows the entire 16S rDNA sequence for *C. testosteroni* ATCC No. 11996; *Brachymonas denitrificans* AS-P1, strain A-1, and a partial sequence for the "Stripa-derived" environmental clone. These sequences correspond, respectively, to SEQ ID NOS:1–4. Except for A-1, the sequences in FIG. 2 were retrieved electronically from the Ribosomal Database Project.

Table 1 summarizes the information of FIG. 2, providing a similarity matrix for the sequences. To facilitate the comparisons, the program introduced gaps into the sequences by maximizing the alignment of the highest possible number of identical sequences. The length of 16S rDNA sequence (without gaps) differed somewhat among these bacteria, as shown. The "Stripa-derived" sequence data in the database was determined originally from PCR-amplified rDNA using a DNA template that was extracted directly from an environmental sample. Hence, the organism that gave rise to the "Stripa-derived" DNA was never propagated or cultured; no physiological data are available for it, so its physiological properties could not be compared with those of the filamentous bacteria.

Taken together with the unusual physiological profile of the filamentous bacterium, the data in Table 1 strongly suggest that it is a new species, and may be the first known member of a previously unknown genus. The 16S-rDNA sequence of A-1 differs from the most closely-related match, *C. testosteroni* ATCC No. 11996, at 4.62% of the compared nucleotide residues. This extent of difference is comparable to that observed for other pairs of organisms that are known to be different species. TABLE 1 shows, for example, that *C. testosteroni* ATCC No. 11996 and *B. denitrificans* AS-P1 differ at 5.47% of the residues in the compared region. This degree of difference is comparable to the 4.62% difference between A-1 and *C. testosteroni* ATCC No. 11996. The notion that strain A-1 is at least a new species is particularly compelling in view of the filamentous bacterium's unusual appearance (FIGS. 1A and 1B), which represents a morphology not previously reported for any member of the genus Comamonas.

The sequence data of FIG. 3 suggest further that strain A-1 differs from previously known bacteria. FIG. 3 adds sequences from *Comamonas terrigena* ATCC No. 8461 and *Comamonas acidovorans* ATCC No. 15668 to the sequences shown in FIG. 2 and Table 1. These additional sequences were derived as described in Dyksterhouse et al (1995), using the SP3 primer. Only partial 16S gene sequences were available for these two organisms. Accordingly, to compare it with A-1, the corresponding sequences from the organism listed in FIG. 2 were excerpted and aligned with *C. testosteroni* and *C. acidovorens* sequences as shown in FIG. 3. As for FIG. 2, a computer program was used to facilitate alignment of the sequences. The length of the ungapped fragments used for this comparison was 348 nucleotides for all of the included organisms except for the "Stripa-derived" bacterium, for which it was 263. The sequences of FIG. 3 correspond to SEQ ID NOS:5–10, and were derived, respectively, from *C. testosteroni* ATCC No. 11996, "Stripa-derived" environmental clone, strain A-1, *Brachymonas denitrificans* AS-P1, *C. terrigena* ATCC No. 8461, and *C. acidovorans* ATCC No. 15668.

Table 2 summarizes the sequences shown in FIG. 3, and provides a similarity matrix for the six organisms whose sequences are compared. Table 2 indicates that for this region of the 16S rDNA sequence, the degree of difference between strain A-1 and the other microorganisms analyzed ranged from 4.18% to 10.92%. These differences exceed the differences seen between most pairs of organisms included in Table 2, again suggesting strongly that strain A-1 represents at least a new species of bacteria.

Example 4

Accumulation of Intracellular Poly-β-Hydroxybutyrate (PHB) by Strain A-1

Under the light microscope, the filamentous bacterium presents a characteristic granular appearance. Phase contrast microscopy revealed that the filaments of strain A-1 contain optically retractile inclusion bodies. Transmission electron micrographs also showed abundant large inclusions. Staining results suggested that these inclusions are comprised of PHB and possibly polyphosphate. When the culture was grown under nitrogen-limiting conditions, up to 80% of the culture dry weight was indeed determined to be PHB by gas chromatographic analysis.

Example 5

Degradation of TCE

In these experiments, TCE degradation was measured using methods previously described (Folsom et al., 1990; Bielefeldt et al., 1995). In brief, TCE degradation was measured by extracting aliquots of the culture with pentane, and analyzing by gas chromatography. Concentrations of TCE in the samples were determined by comparison with a standard curve.

Under endogenous conditions (i.e., with no inducer such as phenol concurrently present), all cultures of the filamentous bacteria as well as the A-1 isolate degraded TCE over a wide range of substrate concentrations.

For tests with initial TCE concentrations ranging from about 5–25 mg/l, zero-order kinetics for initial degradation rates were observed. Zero-order kinetics were observed also for substrate concentrations as low or lower than 1 mg/L TCE. Rates of TCE consumption ranged from 0.11 to 0.25 g TCE/g VSS-d. In one set of tests, the average TCE consumption rate was 0.18 g/g VSS-d with a standard deviation of 0.033 for 12 tests. There was no significant difference in TCE degradation rates after 0, 8, and 24 h of pre-aeration using NL1, although some rate reduction was observed when NNL was tested. TCE degradation rates decreased at TCE concentrations above 30 mg/L, possibly due to TCE toxicity. Despite the filamentous bacteria's sensitivity to very high TCE concentrations, the consortia tolerated and degraded TCE at concentrations much higher than the 7.7 mg/L maximum tolerable concentration reported for methanotrophs (Strand et al., 1990).

The effect of phenol addition on TCE degradation rate was tested. Bottles that were spiked with 10–40 mg/l of phenol exhibited higher TCE degradation rates than those that did not receive phenol. Over the tested range of phenol concentrations, TCE degradation rates varied but were consistently higher than the average endogenous degradation rates at similar TCE concentrations. The higher degradation rates induced by adding phenol persisted for the duration of the TCE degradation (approximately eight hours), even though the added phenol was degraded completely within about an hour of its addition. Thus, there appeared to be no competitive inhibition of TCE degradation by phenol. Moreover, even at TCE concentrations above 40 mg/L, phenol addition caused a stimulation in the TCE degradation rates.

The capacity of the filamentous bacteria to degrade TCE was further quantified to facilitate comparisons with other organisms. For this purpose, the filamentous bacteria's capacity to degrade TCE was expressed as grams of TCE degraded per gram of cells present, or "transformation quantity (Tq)." Values calculated for Tq ranged from >0.31–0.51. These transformation quantities were higher than the reported values for endogenous batch TCE degradation tests with methanotrophs and phenol-grown mixed cultures (Bielefeldt et al., 1995, Table 4).

To determine whether the filamentous bacteria could degrade TCE when grown in pure culture, tests were performed using strain A-1 grown in batch cultures with phenol as the sole source of carbon. Cells were washed and resuspended in chloride-free media in serum bottles with teflon-valved closures. TCE was added to produce an aqueous concentration of approximately 12 mg TCE/L. Total TCE in each bottle was approximately 3 μM. The rate of TCE degradation was assessed by using standard methods to measure chloride production over a period of several days (Nelson et al., 1987). Results indicated that strain A-1 degraded TCE at a slightly lower rate than those reported for pure *Burkholderia cepacia* G4. These results indicate that even though the filamentous bacteria grows somewhat better in mixed cultures, it is nevertheless capable of degrading TCE without requiring the presence of other bacteria.

Other experiments indicated that the consortia could not degrade tetrachloroethylene, chloroform, and 111-trichloroethane, which were measured also by gas chromatography. However, for unknown reasons a concentration of 5 mg/L of 111-trichloroethane inhibited TCE degradation, although 111-trichloroethane at 1 mg/L did not affect TCE degradation. Neither tetrachloroethylene nor chloroform had any effect on TCE degradation rates at the concentrations tested.

Example 6

Intermediate Toxicity

To determine whether the filamentous bacteria were susceptible to toxic effects from TCE metabolic intermediates seen with other TCE degraders, tests were conducted to compare degradation rates of TCE with and without prior TCE degradation in the same culture sample. The experiment also included tests to determine whether phenol would affect the filamentous bacterium's reaction to possible toxic effects of TCE breakdown products. Four culture bottles were used for this test. Two were initially spiked with about 25 mg/L TCE to generate intermediates, while two other bottles were put into the shaker without TCE. After 24 h, one TCE-fed culture was respiked with 25 mg/L TCE, and the other with 25 mg/L TCE plus 20 mg/L phenol. Also after 24 h, one of the remaining two cultures that had not been fed TCE was spiked with 25 mg/L TCE, and the other spiked with 25 mg/L TCE plus 20 mg/L phenol.

No effects of intermediate toxicity were seen, as the samples with prior exposure to TCE actually degraded the second dose of TCE at a slightly faster rate than their counterparts that were not pre-exposed to TCE. Faster degradation of the second dose of TCE was observed whether or not the second dose was accompanied by a dose of phenol. When the initial doses of TCE were increased up to 0.51 g TCE/g cells, still no toxic effects were observed. Moreover, no toxic effects were observed when similar tests were conducted with DCE instead of TCE, at loadings of DCE up to 0.3 g DCE/g cells (see Example 7). It was noted also that bottles respiked with phenol degraded TCE at a rate about three times higher than the cultures that did not receive the dose of phenol.

Example 7

Degradation of DCE

The enrichment cultures were tested for their ability to degrade DCE under endogenous conditions using the methods previously described (Bielefeldt et al., 1995). DCE concentration was analyzed by purge and trap gas chromatography with a Hall detector in which samples were purged 10 minutes with a 3-minute desorb time and 5-minute bake time. With initial DCE concentrations ranging from 14–83 mg/L, zero order kinetics were observed for DCE degradation under endogenous conditions. At the highest initial concentration tested, no significant decrease in initial degradation rate was evident in comparison with the lower concentrations tested concurrently. The initial degradation rates observed for DCE exceeded those observed for TCE degradation. When cultures were spiked with phenol, the observed rates of DCE degradation were 2–6-times higher than in the absence of phenol.

To determine whether intermediates of DCE metabolism were toxic to the filamentous bacteria, DCE degradation rates with and without prior DCE degradation were compared using DCE respiking tests (Bielefeldt et al., 1995). Several batch cultures from the NLL consortium were allowed to degrade an initial dose of DCE to completion, then respiked with a second dose eight hours after the first dose. The first dose was degraded at a rate of 0.85 g DCE/g VSS-d, and the second dose at a rate of 0.10 g DCE/g VSS-d. Thus, the second dose of DCE was degraded more slowly than the first. However, a control batch culture that received only the second dose of DCE also degraded it at a rate of 0.10 g DCE/g VSS-d. Thus, these results with the control cultures indicated that the prior degradation of DCE had had no effect on the later DCE degradation rate, indicating no intermediate toxicity. Instead, the decrease in degradation rate for the second dose of DCE most likely can be attributed to endogenous depletion of energy reserves.

Further, if intermediate toxicity had significantly affected the cells, the addition of phenol would not have been expected to increase the rate because the cells would have been damaged and unable to utilize the electron donor. However, in experiments where phenol was added with the second dose of DCE, the culture's ability to degrade DCE was largely restored.

In other experiments, it was observed that there was no decline in the degradation rate of either compound during the concurrent degradation of TCE and DCE by the enrichment cultures.

Example 8

Screening Test to Confirm the Identity of Field Isolates of Filamentous Phenol Degrading Bacteria The nucleotide sequences shown in SEQ ID NO:3 and SEQ ID NO:7 are used as the basis for designing oligonucleotide probes for a hybridization-based confirmation test. Probe design is based on information presently available in the prior art. The secondary structure of prokaryotic 16S rRNA has been elucidated and within this relatively invariant structure, several regions have been mapped within which the degree of sequence variability among species is relatively high (e.g., Autell and Fox, 1988, which is hereby incorporated by reference). These are known as "hypervariable regions." Other authors have disclosed methods of constructing phylogenetic trees by using a computer to align 16S rRNA sequences from different prokaryotes (Olsen et al., 1986). Such alignments make it possible to locate these hypervariable regions within any bacterial 16S rRNA sequence, given the demonstrated consistency of their locations. For example, hypervariable region probes have been used to successfully determine phylogenetic relationships by several different investigators (e.g., Moncla et al., 1990; Chuba et al., 1988; Göbel et al., 1987). Hence, one skilled in the art can readily identify the hypervariable regions of strain A-1 by aligning the sequences in SEQ ID NO:3 with previously determined bacterial 16S rRNA sequences. Oligonucleotide probes based on these sequences are used in diagnostic confirmation tests for field isolates of the filamentous bacterium.

Probes corresponding to the hypervariable regions of strain A-1's 16S rRNA are synthesized by reference to SEQ ID NO:3 and the published literature (e.g., Noller, 1984; Moncla et al., 1990;; Göbel et al., 1987; Chuba et al., 1988; Autell and Fox, 1988; Olsen et al., 1986; Woese, 1987). Standard methodologies are applied to select the best probes and the optimum hybridization conditions for distinguishing the filamentous bacteria of the subject invention from other bacteria. Probes that are capable of differentiating strain A-1 from its nearest relatives are used for screening new isolates of filamentous phenol-degrading bacteria to determine whether they belong to the same phylogenetic position as the filamentous bacterium of the present invention.

For determining the optimum hybridization conditions, filters are loaded with DNA extracted from strain A-1, as well as DNA from those bacteria that are known to be most closely related to the filamentous bacteria, namely *Comamonas acidovorans, Comamonas testosteroni* and *Brachymonas dentrificans.* Filters or membranes are also loaded with DNAs from distantly-related bacteria, such as *Escherichia coli.* A number of replicates of such membranes are prepared and used to test oligonucleotide probes based on the nucleotide regions shown in SEQ ID NO:3. The object of the tests is to identify probes that provide the requisite sensitivity and selectivity for distinguishing the filamentous bacteria from other known bacteria. Oligonucleotide probes are synthesized using a DNA synthesizer following the procedures provided by the manufacturer, and labeled with either a radioactive or nonradioactive reporter molecule. In choosing sequences for candidate oligonucleotide probes, probes are chosen based on the prior art and that contain the highest possible number of bases at which the sequence for A-1 differs from the organisms shown in Tables 1 and 2. Using conventional techniques (e.g., see Sambrook et al., 1989), probes are radioactively labeled or labeled with a nonradioactive reporter molecule that will fluoresce or produce a colored product. Each labeled probe is hybridized under stringent conditions with one of the replicate filter strips. Probes that hybridize with strain A-1 DNA but not with DNA from the other bacteria are deemed to have the requisite specificity for differentiating the filamentous bacteria of the subject invention from other bacteria.

The length of the probes is chosen using criteria based on established methodology in the prior art. Ten nucleotides is generally the lower limit for useful oligonucleotides because shorter probes sometimes cannot form stable hybrid duplexes regardless of hybridization conditions. Probes of about 20–30 nucleotides in length are preferred, as such probes are far more likely to form stable duplexes with their complementary sequences and, moreover, are very likely to be disruptable by mismatched bases. Sequences of this length are extremely unlikely to occur by chance anywhere within a bacterial genome.

The probes are tested to determine whether each candidate probe provides the required specificity, i.e., the ability to form a stable duplex with strain A-1 DNA but not with DNA from *C. testosteroni, C. acidovorans,* or *B. dentrificans* or other non-filamentous bacteria. Stringent hybridization conditions are generally understood to mean conditions that permit only perfectly matched or nearly perfectly matched hybrids to form. The use of such conditions will facilitate identification of probes that hybridize specifically with 16S rDNA of the filamentous bacteria. However, the stability of duplexes formed with oligonucleotide probes can sometimes be disrupted by even a single mismatched base pair (Wallace et al., 1979; Wallace et al., 1981). The destabilizing effects on the duplex of mismatched bases becomes greater as probe length decreases so that for very short probes, for example, those shorter than 20 nucleotides, stringent hybridization conditions will rarely tolerate any mismatched bases. For longer probes, e.g., those >50 bases long, a small number of mismatches may be tolerated even under stringent conditions. However, the procedures provided here nonetheless can identify probes having the requisite specificity even if such probes form stable duplexes containing a small number of mismatched bases. This is because the probe testing procedure identifies probes that react with strain A-1 DNA and not with the DNA from the other bacteria present on the filter. Probes meeting this criterion by definition have the requisite specificity to be used in the confirmation assay for testing new isolates of the filamentous bacterium. Hence, it is immaterial for the purposes of this assay whether the probes chosen for use form perfect or nearly perfect hybrids, as the ability to distinguish strain A-1 from the other bacteria on the filter is the only pertinent quality required for a test probe useful in the screening assay.

A variety of useful hybridization conditions are available in the published literature (Sambrook et al., 1989). For example, it is known that the amount of formamide present in hybridization solutions has a predictable effect on the stringency of hybridization reactions. By varying the percentage of formamide present, one can vary the percentage of mismatched bases that will be tolerated in duplexes that form at a given incubation temperature. To determine the optimal hybridization conditions for the probes for the present screening assay, a series of hybridization reactions is conducted with the replicate filters described above. Each filter is hybridized with a different percentage of formamide present in the hybridization solution. The optimal hybridization condition for each probe is that in which the relative signal strengths between strain A-1 DNA and the other DNA on the filter shows the greatest difference. Using the hybridization conditions that provide the greatest relative signal strength differences, or specificity, filters are prepared that contain, in addition to strain A-1 and the Comamonas and Brachymonas DNAs, DNAs from NL1 and NNL in which the filamentous bacterium predominates. Probes that hybridize strongly with DNA from strain A-1, NL1 and NNL but weakly or not at all with the other DNAs on the filter are the test probes used further in screening field isolates of phenol-degrading bacteria. The best probes for this assay are those that hybridize with DNA from the subject filamentous bacteria and not at all with DNA from the other bacteria whose DNA is present on the filter. Probes that hybridize slightly with DNA besides the filamentous bacteria are useful also, provided the signal strength with filamentous bacterial DNA is measurably greater than with the other DNAs. For example, densitometry can be used to quantify signal strength differences.

In the screening test, the signal obtained by hybridizing the test probe with A-1 DNA will be compared with the signal strength obtained when the test probe is hybridized with DNA from the new field isolates. The field isolate is regarded as being within the scope of the present invention when its DNA hybridizes with the test probes to a similar extent as the probes hybridize with A-1 DNA. For the screening test, the filters contain control DNAs as well as DNA from the new isolates. Control DNAs include *C. testosteroni, C. acidovorans, B. dentrificans,* and *E. coli* DNAs, and other DNAs if desired. Thus, the reagents provided here, when combined with conventional methodology, are readily used to develop a rapid screening test to verify the identity of any field isolate of a phenol-degrading filamentous bacteria.

Example 9

Methods for Using the Filamentous Bacterium for Bioremediation

Water or soil carrying TCE or DCE is aerated, and the TCE is transferred to the air stream to which the contaminated water or soil is subjected. The TCE-bearing air stream is passed subsequently through a biofilter or bioreactor in which the subject microorganisms are present. The biofilter or bioreactor is inoculated with a pure culture of strain A-1, or with an aliquot of a consortium in which the filamentous bacteria of the subject invention is the predominant microorganism. The biofilter or bioreactor is supplied with the enrichment medium described in Example 1.

While the preferred embodiment of the invention has been illustrated and described, it will be appreciated that various changes can be made therein without departing from the spirit and scope of the invention.

REFERENCES

1. Ensley, B. D. "Biochemical diversity of trichloroethylene metabolism." *Ann. Rev. Microbiol,* 45:283–299 (1991).
2. Fogel, M. M. et al. "Biodegradation of Chlorinated Ethenes by a Methane-Utilizing Mixed Culture." *Applied and Environ. Microbiol.,* 51(4):720–724 (1986).
3. Alvarez-Cohen, L. and McCarty, P. L. "Effects of Toxicity, Aeration, and Reductant Supply on Trichloroethylene Transformation by a Mixed Methanotrophic Culture." *Appl. and Environ. MicrobioL,* 57:228–235 (1991a).
4. Alvarez-Cohen, L. and McCarty, P. L. "A Cometabolic Biotransformation Model for Halogenated Aliphatic Compounds Exhibiting Product Toxicity." *Environ. Sci. Technol,* 25(8):1381–1386 (1991b).
5. Alvarez-Cohen, L. and McCarty, P. L. "Product Toxicity and Cometabolic Competitive Inhibition Modeling of Chloroform and Trichloroethylene Transformation by Methanotrophic Resting Cells." *Appl. and Environ. Microbiol.,* 57(4):1031–1037 (1991c).
6. Rasche, M. E. et al. *Appl Environ. Microbiol,* 57:2986–2994 (1991).
7. Oldenhuis, R., Vink, R. L. J. M., Janssen, D. B., and Witholt, B. "Degradation of Chlorinated Aliphatic Hydrocarbons by *Methylosinus trichosporium* OB3b Expressing Soluble Methane Monooxygenase." *Appl. and Environ. Microbiol.,* 55:2819–2826 (1989).

8. Strand, S. E., Bjelland, M. D., and Stensel, H. D. "Kinetics of chlorinated hydrocarbon degradation by suspended cultures of methane-oxidizing bacteria." *Research Journal WPCF,* 62:124–129 (1990).

9. U.S. Pat. No. 4,925,802.

10. U.S. Pat. No. 5,071,755.

11. Yabuuchi, E., Kosako, Y., Oyaizu, H., Yano, I., Hotta, H., Hashimoto, Y., Ezaki, T., and M. Arakawa, *Microbiol. Immunol.,* 36:1251–1275 (1992).

12. Folsom, B. R., Chapman, P. R., and Pritchard, P. H. "Phenol and Trichloroethylene Degradation by *Pseudomonas cepacia* G4: Kinetics and Interactions between Substrates." *Appl. and Environ. Microbiol,* 56(5):1279–1285 (1990).

13. Wackett, L. P. and Householder, S. R. "Toxicity of Trichloroethylene to *Pseudomonas putida* F1 Is Mediated by Toluene Dioxygenase." *Appl. and Environ. Microbiol.,* 55:2723–2725 (1989).

14. Hopkins, G. D., Munakata, J., Semprini, L., and McCarty, P. L. "Trichloroethylene concentration effects on pilot field-scale in-situ groundwater bioremediation by phenol-oxidizing microorganisms." *Envir. Sci. Technol.,* 27(12):2542–2547 (1993a).

15. Hopkins, G. D., Semprini, L., and McCarty, P. L. "Microcosm and In Situ Field Studies of Enhanced Biotransformation of Trichloroethylene by Phenol-Utilizing Microorganisms." *Appl. and Environ. MicrobioL,* 59:2277–2285 (1993b).

16. Nelson, M. J. K., Montgomery, S. O., and Pritchard, P. H. "Trichloroethylene Metabolism by Microorganisms that Degrade Aromatic Compounds." *AppL and Environ. MicrobioL,* 54:604–606 (1988).

17. Shields, M. S., Montgomery, S. O., Chapman, P. J., Cruskey, S. M., and Pritchard, P. H. "Novel Pathway of Toluene Catabolism in the Trichloroethylene-Degrading Bacterium G4." *Appl. and Environ. Microbiol.,* 55:1624–1629 (1989).

18. Harker, A. R. and Kim, Y. "Trichloroethylene Degradation by Two Independent Aromatic-Degrading Pathways in *Alcaligenes eutrophus* JMP134." *Appl. and Environ. Microbiol.,* 56:1179–1181 (1990).

19. Bielefeldt et al. "Cometabolic Degradation of TCE and DCE Without Intermediate Toxicity." *J. Environ. Eng.,* 791–797 (November 1995).

20. Woese, C. R., *MicrobioL Rev.,* 51:221–271 (1987).

21. Olsen, G. J. et al. "Microbial Ecology and Evolution: A Ribosomal RNA Approach." *Ann. Rev. Microbiol,* 40:337–365 (1986).

22. Gutell, R. R. et al. "Lessons From an Evolving rRNA: 16S and 23S rRNA Structures From a Comparative Perspective." *Microbiological Reviews,* 58:10–26 (1994).

23. Olsen, G. J. et al. "The Winds of (evolutionary) Change: Breathing New Life Into Microbiology." *J Bacteriol.,* 176:1–6 (1994).

24. Moncla, B. -J. et al. "Use of Synthetic Oligonucleotide DNA Probes for the Identification of *Bacteroides gingivalis." J Clin. Microbiol.,* 28(2):324–327 (1990).

25. Sambrook, J., Fritsch, E. F., and Mariates, T. Molecular Cloning, Second Ed., Cold Spring Harbor Press (1989).

26. Dyksterhouse, S. E. et al. "*Cycloclasticus pugetii* gen. nov., sp. nov., an Aromatic Hydrocarbon-Degrading Bacterium from Marine Sediments." *Intl. J Systematic Bacteriology,* 45(1): 116–123 (1995).

27. U.S. Pat. No. 5,120,652.

28. Nelson, M. J. K., Montgomery, S. O., Mahaffey, W. R., and Pritchard, P. H. "Biodegradation of Trichloroethylene and Involvement of an Aromatic Biodegradative Pathway." *Appl. and Environ. Microbiol.,* 53:949–954 (1987).

29. Autell, R. R. and Fox, A. E. *Nucl. Ac. Res.,* 16(suppl.) :175 (1988).

30. Chuba, P. et al. *J General Microbiology,* 134:1931–1938 (1988).

31. Göbel, U. et al. *Israel J Med. Sci.,* 23:742–746 (1987).

32. Noller, H. F. *Ann. Rev. Biochem.,* 53:119–162 (1984).

33. Wallace, R. B. et al., *Nucleic Acids Res.,* 6:3543–3557 (1979).

34. Wallace, R. B. et al., *Nucleic Acids Res.,* 9:879–895 (1981).

We claim:

1. In a method of bioremediation comprising contacting an environmental sample contaminated with chlorinated aliphatic compounds with a bacterium capable of metabolizing chlorinated aliphatic compounds in the environmental sample, wherein the improvement comprises contacting the environmental sample with a bacterium having non-sheathed rod-shaped cells filamentous in appearance and ranging in length from 20–200 $\mu$m, and that is aerobic, gram-negative, that under nitrogen-limiting conditions accumulates intracellular poly-β-hydroxybutyrate in intracellular granules, that is capable of growing in the presence of 0.2% phenol or 1% saturated toluene vapor, and that does not grow on carbohydrates.

2. The method of claim 1, wherein the environmental sample is selected from among soil, water, and air samples.

3. The method of claim 1, wherein the bacterium has a 16S ribosomal DNA comprising a nucleotide sequence substantially identical to the sequence depicted in SEQ ID NO:3.

4. The method of claim 1, wherein the bacterium has a 16S ribosomal DNA comprising a nucleotide sequence substantially identical to the sequence depicted in SEQ ID NO:7.

5. The method of claim 1, wherein the bacterium is ATCC No. 55581.

6. In a method of bioremediation comprising selecting from among soil and water an environmental sample contaminated with chlorinated aliphatic compounds, contacting the environmental sample with a stream of air into which the chlorinated aliphatic compounds are transferred, and contacting the chlorinated aliphatic compound-bearing air with a bacterium capable of metabolizing chlorinated aliphatic compounds, wherein the improvement comprises contacting the chlorinated aliphatic compound-bearing air with a bacterium having non-sheathed rod-shaped cells, and that is aerobic, gram-negative, filamentous, that under nitrogen-limiting conditions accumulates intracellular poly-β-hydroxybutyrate in intracellular granules, that is capable of growing in the presence of 0.2% phenol or 1% saturated toluene vapor, and that does not grow on carbohydrates.

* * * * *

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
( A ) LENGTH: 1536 base pairs
( B ) TYPE: nucleic acid
( C ) STRANDEDNESS: single
( D ) TOPOLOGY: linear ( i i ) MOLECULE TYPE: nucleic acid
( A ) DESCRIPTION: "16S ribosomal DNA"

( i i i ) HYPOTHETICAL: NO ( i v ) ANTI-SENSE: NO ( v i ) ORIGINAL SOURCE:
( A ) ORGANISM: Comamonas testosteroni ATCC No. 11996

-continued ( x i ) SEQUENCE DESCRIPTION: SEQ ID NO:1:

CGAACTATAG AGTTTGATCC TGGCTCAGAT TGAACGCTGG CGGCATGCTT TACACATGCA 60

AGTCGAACGG TAACAGGTCT TCGGATGCTG ACGAGTGGCG AACGGGTGAG TAATACATCG 120

GAACGTGCCT AGTAGTGGGG GATAACTACT CGAAAGAGTA GCTAATACCG CATGAGATCT 180

ACGGATGAAA GCAGGGGACC TTCGGGCCTT GTGCTACTAG AGCGGCTGAT GGCAGATTAG 240

GTAGTTGGTG GGGTAAAGGC TTACCAAGCC TGCGATCTGT AGCTGGTCTG AGAGGACGAC 300

CAGCCACACT GGGACTGAGA CACGGCCCAG ACTCCTACGG GAGGCAGCAG TGGGGAATTT 360

TGGACAATGG GCGAAAGCCT GATCCAGCAA TGCCGCGTGC AGGATGAAGG CCCTCGGGTT 420

GTAAACTGCT TTTGTACGGA ACGAAAAGCC TGGGGCTAAT ATCCCCGGGT CATGACGGTA 480

CCGTAAGAAT AAGCACCGGC TAACTACGTG CCAGCAGCCG CGGTAATACG TAGGGTGCAA 540

GCGTTAATCG GAATTACTGG GCGTAAAGCG TGCGCAGGCG GTTTTGTAAG ACAGTGGTGA 600

AATCCCCGGG CTCAACCTGG GAACTGCCAT TGTGACTGCA AGGCTAGAGT GCGGCAGAGG 660

GGGATGGAAT TCCGCGTGTA GCAGTGAAAT GCGTAGATAT GCGGAGGAAC ACCGATGGCG 720

AAGGCAATCC CCTGGGCCTG CACTGACGCT CATGCACGAA AGCGTGGGGA GCAAACAGGA 780

TTAGATACCC TGGTAGTCCA CGCCCTAAAC GATGTCAACT GGTTGTTGGG TCTTAACTGA 840

CTCAGTAACG AAGCTAACGC GTGAAGTTGA CCGCCTGGGG AGTACGGCCG CAAGGTTGAA 900

ACTCAAAGGA ATTGACGGGG ACCCGCACAA GCGGTGGATG ATGTGGTTTA ATTCGATGCA 960

ACGCGAAAAA CCTTACCCAC CTTTGACATG GCAGGAACTT ACCAGAGATG GTTTGGTGCT 1020

CGAAAGAGAA CCTGCACACA GGTGCTGCAT GGCTGTCGTC AGCTCGTGTC GTGAGATGTT 1080

GGGTTAAGTC CCGCAACGAG CGCAACCCTT GCCATTAGTT GCTACATTCA GTTGAGCACT 1140

CTAATGGGAC TGCCGGTGAC AAACCGGAGG AAGGTGGGGA TGACGTCAAG TCCTCATGGC 1200

CCTTATAGGT GGGGCTACAC ACGTCATACA ATGGCTGGTA CAAAGGGTTG CCAACCCGCG 1260

AGGGGGAGCT AATCCCATAA AGCCAGTCGT AGTCCGGATC GCAGTCTGCA ACTCGACTGC 1320

GTGAAGTCGG AATCGCTAGT AATCGTGGAT CAGAATGTCA CGGTGAATAC GTTCCCGGGT 1380

CTTGTACACA CCGCCCGTCA CACCATGGGA GCGGGTCTCG CCAGAAGTAG GTAGCCTAAC 1440

CGTAAGGAGG GCGCTTACCA CGGCGGGGTT CGTGACTGGG GTGAAGTCGT AACAAGGTAG 1500

CCGTATCGGA AGGTGCGGCT GGATCACCTC CTTTCT 1536

( 2 ) INFORMATION FOR SEQ ID NO:2:

( i ) SEQUENCE CHARACTERISTICS:
( A ) LENGTH: 1452 base pairs
( B ) TYPE: nucleic acid
( C ) STRANDEDNESS: single
( D ) TOPOLOGY: linear ( i i ) MOLECULE TYPE: nucleic acid
( A ) DESCRIPTION: “16S ribosomal DNA”

( i i i ) HYPOTHETICAL: NO ( i v ) ANTI-SENSE: NO ( v i ) ORIGINAL SOURCE:
( A ) ORGANISM: Brachymonas denitrificans AS-P1

( x i ) SEQUENCE DESCRIPTION: SEQ ID NO:2:

ATTGAACGCT GGCGGCATGC TTTACACATG CAAGTCGAAC GGTAACAGGT CCTTCGGATG 60

CTGACGAGTG GCGAACGGGT GAGTAATGTA TCGGAACGTG CCCAGTAGTG GGGGATAACT 120

-continued

```
ACTCGAAAGA GTGGCTAATA CCGCATGAGA ACTGAGGTTG AAAGCGGGGG ACCTTTGGGC   180
CTCGCGCTAC TGGAGCGGCC GATATCAGAT TAGGTAGTTG GTGGGGTAAA GGCCTACCAA   240
GCCGACGATC TGTAGCTGGT CTGAGAGGAC GACCAGCCAC ACTGGGACTG AGACACGGCC   300
CAGACTCCTA CGGGAGGCAG CAGTGGGGAA TTTTGGACAA TGGACGCAAG TCTGATCCAG   360
CAATGCCGCG TGCAGGACGA AGGCCTTCGG GTTGTAAACT GCTTTTGTAC AGAACGAAAA   420
GGCTCTGGTT AATACCTGGG GCTCATGACG GTACTGTAAG AATAAGCACC GGCTAACTAC   480
GTGCCAGCAG CCGCGGTAAT ACGTAGGGTG CGAGCGTTAA TCGGAATTAC TGGGCGTAAA   540
GCGTGCGCAG GCGGTTTTGT AAGACCGATG TGAAATCCCC GGGCTCAACC TGGGAACTGC   600
ATTGGTGACT GCAAGGCTGG AGTGCGGCAG AGGGGGATGG AATTCCGCGT GTAGCAGTGA   660
AATGCGTAGA TATGCGGAGG AACACCGATG GCGAAGGCAA TCCCCTGGGC CTGCACTGAC   720
GCTCATGCAC GAAAGCGTGG GGAGCAAACA GGATTAGATA CCCTGGTAGT CCACGCCCTA   780
AACGATGTCA ACTGGTTGTT GGGTATTTGC TTACTCAGTA ACGAAGCTAA CGCGTGAAGT   840
TGACCGCCTG GGGAGTACGG CCGCAAGGTT GAAACTCAAA GGAATTGACG GGGACCCGCA   900
CAAGCGGTGG ATGATGTGGT TTAATTCGAT GCAACGCGAA AAACCTTACC CACCTTTGAC   960
ATGGCAGGAA TTCCGAAGAG ATTTGGAAGT GCTCGTAAGA GAACCTGCAC ACAGGTGCTG  1020
CATGGCTGTC GTCAGCTCGT GTCGTGAGAT GTTGGGTTAA GTCCCGCAAC GAGCGCAACC  1080
CTTGCCATTA GTTGCTACGA AAGGGCACTC TAATGGGACT GCCGGTGACA AACCGGAGGA  1140
AGGTGGGGAT GACGTCAAGT CCTCATGGCC CTTATAGGTG GGCTACACA CGTCATACAA   1200
TGGCCGGTAC AAAGGGTAGC CAACCCGCGA GGGGGAGCCA ATCCCATAAA GCCGGTCGTA  1260
GTCCGGATCG CAGTCTGCAA CTCGACTGCG TGAAGTCGGA ATCGCTAGTA ATCGTGGATC  1320
AGCATGTCAC GGTGAATACG TTCCCGGGTC TTGTACACAC CGCCCGTCAC ACCATGGGAG  1380
CGGGTTCTGC CAGAAGTGGT TAGCCTAACC GTAAGGAGGG CGATCACCAC GGCAGGGTTC  1440
GTGACTGGGG TG                                                      1452
```

( 2 ) INFORMATION FOR SEQ ID NO:3:

( i ) SEQUENCE CHARACTERISTICS:
( A ) LENGTH: 1455 base pairs
( B ) TYPE: nucleic acid
( C ) STRANDEDNESS: single
( D ) TOPOLOGY: linear ( i i ) MOLECULE TYPE: nucleic acid
( A ) DESCRIPTION: "16S ribosomal DNA"

( i i i ) HYPOTHETICAL: NO ( i v ) ANTI-SENSE: NO ( v i ) ORIGINAL SOURCE:
( A ) ORGANISM: Unknown. Possibly new species
( B ) STRAIN: A-1

( x i ) SEQUENCE DESCRIPTION: SEQ ID NO:3:

```
ATTGAACGCT GGCGGCATGC TTTACACATG CAAGTCGAAC GGCAGCATGG GCTTCGGCCT    60
GATGGCGAGT GGCGAACGGG TGAGTAATAC ATCGGAACGT GCCTGGTAGT GGGGGATAAC   120
TACTCGAAAG AGTAGCTAAT ACCGCATGAG ATCTACGGAT GAAAGCGGGG GATCGCAAGA   180
CCTCGCGCTA CCAGAGCGGC TGGTGGCAGA TTAGGTAGTT GGTGGGATAA AAGCTTACCA   240
AGCCGACGAT CTGTAGCTGG TCTGAGAGGA CGACCAGCCC ACACTGGGAC TGAGACWCGG   300
CCCAGACTCC TACGGGAGGC AGCAGTGGGG AATTTTGGAC AATGGGCGCA AGCCTGATCC   360
```

-continued

| | | | | | | |
|---|---|---|---|---|---|---|
| AGCAATGCCG | CGTNGCAGGA | TGAAGGCCTT | CGGGTTGTAA | ACTGCTTTTG | TACGGAACGA | 420 |
| AAAGGCTCTC | TCTAATACAG | AGAGCCGATG | ACGGTACCGT | AAGAATAAGC | ACCGGCTAAC | 480 |
| TACGTGCCAG | CAGCCGCGGT | AATACGTAGG | GTGCAAGCGT | TAATCGGAAT | TACTGGGCGT | 540 |
| AAAGCGTGCG | CAGGCGGTCT | TGTAAGACAG | AGGTGAAATC | CCCGGGCTCA | ACCTGGGAAC | 600 |
| GGCCTTTGTG | ACTGCAAGGC | TGGAGTGCGG | CAGAGGGGGA | TGGAATTCCG | CGTGTAGCAG | 660 |
| TGAAATGCGT | AGATATGCGG | AGGAACACCG | ATGGCGAAGG | CAATCCCCTG | GGCCTGCACT | 720 |
| GACGCTCATG | CACGAAAGCG | TGGGGAGCAC | ACAGGATTAG | ATACCCTGGT | AGTCCACGCC | 780 |
| CTAAACGATG | TCANCTGGTT | GTTGGGTCTT | CACTGACTCA | GTAACGAAGC | TAACGCGTGA | 840 |
| AGTTGACCGC | CTGGGGAGTA | CGGCCGCAAG | GTTGAAACTC | AAAGGAATTG | ACGGGGACCC | 900 |
| GCACAAGCGG | TGGATGATGT | GGTTTAATTC | GATGCAACGC | GAAAAACCTT | ACCCACCTTT | 960 |
| GACATGGCAG | GAATCCTTTA | GAGATAGAGG | AGTGCTCGAA | AGAGAACCTG | CACACAGGTG | 1020 |
| CTGCATGGCT | GTCGTCAGCT | CGTGTCGTGA | GATGTTGGGT | TAAGTCCCGC | AACGAGCGCA | 1080 |
| ACCCTTGCCA | TTAGTTGCTA | CGAAAGGGCA | CTCTAATGGG | ACTGCCGGTG | ACAAACCGGA | 1140 |
| GGAAGGTGGG | GATGACGTCA | AGTCCTCATG | GCCCTTATAG | GTGGGGCTAC | ACACGTCATA | 1200 |
| CAATGGCTGG | TACAAAGGGT | TGCCAACCCG | CGAGGGGGAG | CCAATCCCAT | AAAGCCAGTC | 1260 |
| GTAGTCCGGA | TCGCAGTCTG | CAACTCGACT | GCGTGAAGTC | GGAATCGCTA | GTAATCGTGG | 1320 |
| ATCAGAATGT | CACGGTGAAT | ACGTTCCCGG | GTCTTGTACA | CACCGCCCGT | CACACCATGG | 1380 |
| GAGCGGGTCT | CGCCAGAAGT | AGGTAGCCTA | ACCGCAAGGA | GGGCGCTTAC | CACGGCGGGG | 1440 |
| TTCGTGACTG | GGGTG | | | | | 1455 |

( 2 ) INFORMATION FOR SEQ ID NO:4:

( i ) SEQUENCE CHARACTERISTICS:
( A ) LENGTH: 876 base pairs
( B ) TYPE: nucleic acid
( C ) STRANDEDNESS: single
( D ) TOPOLOGY: linear ( i i ) MOLECULE TYPE: nucleic acid
( A ) DESCRIPTION: "16S ribosomal DNA"

( i i i ) HYPOTHETICAL: NO ( i v ) ANTI-SENSE: NO ( v i ) ORIGINAL SOURCE:
( A ) ORGANISM: Stripa research mine environmental clone.

( x i ) SEQUENCE DESCRIPTION: SEQ ID NO:4:

| | | | | | | |
|---|---|---|---|---|---|---|
| GCGGTAATAC | GTAGGGTGCA | AGCGTTAATC | GGAATTACTG | GGCGTAAAGC | GTGCGCAGGC | 60 |
| GGTGATGTAA | GACAGGCGTG | AAATCCCCGG | GCTCAACCTG | GGAATTGCGC | TTGTGACTGC | 120 |
| ATCGCTGGAG | TGCGGCAGAG | GGGGATGGAA | TTCCGCGTGT | AGCAGTGAAA | TGCGTAGATA | 180 |
| TGCGGAGGAA | CACCGATGGC | GAAGGCAATC | CCCTGGGCCT | GCACTGACGC | TCATGCACGA | 240 |
| AAGCGTGGGG | AGCAAACAGG | ATTAGATACC | CTGGTAGTCC | ACGCCCTAAA | CGATGTCAAC | 300 |
| TGGTTGTTTG | GGTCTCTTTC | TGACTCAGTA | ACGAGCTAAC | GCGTGAAGTT | GACCGCCTGG | 360 |
| GGAGTACGGC | CGCAAGGTTG | AAACTCAAAG | GAATTGACGG | GGACCCGCAC | AAGCGGTGGA | 420 |
| TGATGTGGTT | TAATTCGATG | CAACGCGAAA | AACCTTACCC | ACCTTTGACA | TGTACGGAAT | 480 |
| TTGCCAGAGA | TGGCTTAGTG | CTCGAAAGAG | AGCCGTAACA | CAGGTGCTGC | ATGGCTGTCG | 540 |
| TCAGCTCGTG | TCGTGAGATG | TTGGGTTAAG | TCCCGCAACG | AGCGCAACCC | TTGTCATTAG | 600 |
| TTGCTACATT | CAGTTGGGCA | CTCTAATGAG | ACTGCCGGTG | ACAAGCCGGA | GGAAGGTGGG | 660 |

-continued

```
GATGACGTCA AGTCCTCATG GCCCTTATAG GTGGGGCTAC ACACGTCATA CAATGGCCGG      720

TACAAAGGGT CGCAAACCCG CGAGGGGGAG CCAATCCATC AAAGCCGGTC GTAGTCCGGA      780

TCGCAGTCTG CAACTCGACT GCGTGAAGTC GGAATCGCTA GTAATCGTGG ATCAGCATGT      840

CACGGTGAAT ACGTTCCCGG GTCTTGTACA CACCGC                                876
```

( 2 ) INFORMATION FOR SEQ ID NO:5:

( i ) SEQUENCE CHARACTERISTICS:
( A ) LENGTH: 348 base pairs
( B ) TYPE: nucleic acid
( C ) STRANDEDNESS: single
( D ) TOPOLOGY: linear ( i i ) MOLECULE TYPE: nucleic acid
( A ) DESCRIPTION: "16S ribosomal DNA"

( i i i ) HYPOTHETICAL: NO ( i v ) ANTI-SENSE: NO ( v i ) ORIGINAL SOURCE:
( A ) ORGANISM: Comamonas testosteroni ATCC No. 11996

( x i ) SEQUENCE DESCRIPTION: SEQ ID NO:5:

```
TACGGAACGA AAAGCCTGGG GCTAATATCC CCGGGTCATG ACGGTACCGT AAGAATAAGC       60

ACCGGCTAAC TACGTGCCAG CAGCCGCGGT AATACGTAGG GTGCAAGCGT TAATCGGAAT      120

TACTGGGCGT AAAGCGTGCG CAGGCGGTTT TGTAAGACAG TGGTGAAATC CCCGGGCTCA      180

ACCTGGGAAC TGCCATTGTG ACTGCAAGGC TAGAGTGCGG CAGAGGGGGA TGGAATTCCG      240

CGTGTAGCAG TGAAATGCGT AGATATGCGG AGGAACACCG ATGGCGAAGG CAATCCCCTG      300

GGCCTGCACT GACGCTCATG CACGAAAGCG TGGGGAGCAA ACAGGATT                   348
```

( 2 ) INFORMATION FOR SEQ ID NO:6:

( i ) SEQUENCE CHARACTERISTICS:
( A ) LENGTH: 263 base pairs
( B ) TYPE: nucleic acid
( C ) STRANDEDNESS: single
( D ) TOPOLOGY: linear ( i i ) MOLECULE TYPE: nucleic acid
( A ) DESCRIPTION: "16S ribosomal DNA"

( i i i ) HYPOTHETICAL: NO ( i v ) ANTI-SENSE: NO ( v i ) ORIGINAL SOURCE:
( A ) ORGANISM: Unknown. Stripa research mine environmental clone.

( x i ) SEQUENCE DESCRIPTION: SEQ ID NO:6:

```
GCGGTAATAC GTAGGGTGCA AGCGTTAATC GGAATTACTG GGCGTAAAGC GTGCGCAGGC       60

GGTGATGTAA GACAGGCGTG AAATCCCCGG GCTCAACCTG GGAATTGCGC TTGTGACTGC      120

ATCGCTGGAG TGCGGCAGAG GGGGATGGAA TTCCGCGTGT AGCAGTGAAA TGCGTAGATA      180

TGCGGAGGAA CACCGATGGC GAAGGCAATC CCCTGGGCCT GCACTGACGC TCATGCACGA      240

AAGCGTGGGG AGCAAACAGG ATT                                              263
```

( 2 ) INFORMATION FOR SEQ ID NO:7:

( i ) SEQUENCE CHARACTERISTICS:
( A ) LENGTH: 348 base pairs
( B ) TYPE: nucleic acid -continued ( C ) STRANDEDNESS: single
( D ) TOPOLOGY: linear ( i i ) MOLECULE TYPE: nucleic acid
( A ) DESCRIPTION: "16S ribosomal DNA"

( i i i ) HYPOTHETICAL: NO ( i v ) ANTI-SENSE: NO ( v i ) ORIGINAL SOURCE:
( A ) ORGANISM: Unknown. Possibly new species.
( B ) STRAIN: A-1

( x i ) SEQUENCE DESCRIPTION: SEQ ID NO:7:

```
TACGGAACGA AAAGGCTCTC TCTAATACAG AGAGCCGATG ACGGTACCGT AAGAATAAGC    60
ACCGGCTAAC TACGTGCCAG CAGCCGCGGT AATACGTAGG GTGCAAGCGT TAATCGGAAT   120
TACTGGGCGT AAAGCGTGCG CAGGCGGTCT TGTAAGACAG AGGTGAAATC CCCGGGCTCA   180
ACCTGGGAAC GGCCTTTGTG ACTGCAAGGC TGGAGTGCGG CAGAGGGGGA TGGAATTCCG   240
CGTGTAGCAG TGAAATGCGT AGATATGCGG AGGAACACCG ATGGCGAAGG CAATCCCCTG   300
GGCCTGCACT GACGCTCATG CACGAAAGCG TGGGGAGCAC ACAGGATT                348
```

( 2 ) INFORMATION FOR SEQ ID NO:8:

( i ) SEQUENCE CHARACTERISTICS:
( A ) LENGTH: 348 base pairs
( B ) TYPE: nucleic acid
( C ) STRANDEDNESS: single
( D ) TOPOLOGY: linear ( i i ) MOLECULE TYPE: nucleic acid
( A ) DESCRIPTION: "16S ribosomal DNA"

( i i i ) HYPOTHETICAL: NO ( i v ) ANTI-SENSE: NO ( v i ) ORIGINAL SOURCE:
( A ) ORGANISM: Brachymonas denitrificans AS-P1

( x i ) SEQUENCE DESCRIPTION: SEQ ID NO:8:

```
TACAGAACGA AAAGGCTCTG GTTAATACCT GGGGCTCATG ACGGTACTGT AAGAATAAGC    60
ACCGGCTAAC TACGTGCCAG CAGCCGCGGT AATACGTAGG GTGCGAGCGT TAATCGGAAT   120
TACTGGGCGT AAAGCGTGCG CAGGCGGTTT TGTAAGACCG ATGTGAAATC CCCGGGCTCA   180
ACCTGGGAAC TGCATTGGTG ACTGCAAGGC TGGAGTGCGG CAGAGGGGGA TGGAATTCCG   240
CGTGTAGCAG TGAAATGCGT AGATATGCGG AGGAACACCG ATGGCGAAGG CAATCCCCTG   300
GGCCTGCACT GACGCTCATG CACGAAAGCG TGGGGAGCAA ACAGGATT                348
```

( 2 ) INFORMATION FOR SEQ ID NO:9:

( i ) SEQUENCE CHARACTERISTICS:
( A ) LENGTH: 348 base pairs
( B ) TYPE: nucleic acid
( C ) STRANDEDNESS: single
( D ) TOPOLOGY: linear ( i i ) MOLECULE TYPE: nucleic acid
( A ) DESCRIPTION: "16S ribosomal DNA"

( i i i ) HYPOTHETICAL: NO ( i v ) ANTI-SENSE: NO ( v i ) ORIGINAL SOURCE:
( A ) ORGANISM: Comamonas terrigena ATCC No. 8461

-continued ( x i ) SEQUENCE DESCRIPTION: SEQ ID NO:9:

```
TACGGAACGA AAAGCTTCGG GTTAATACCC TGGAGTCATG ACGGNACCGT AAGAATAAGC  60
ACCGTNTAAC TACGTGCCAG CAGCCGCGGT AATACGTAGG GTNCAAGCGT TANTCGGNAT 120
TACTGGGCGT AAAGCGTGCG CAGGCGGTCT TGTAAGACAG AGGTGANNTC CCCGGNCTCA 180
NCCTGGGAAC TGCCTNTGTG ACTACAAGGC TGGAGTGCGG NAGAGGGGGA TCGANTTCCG 240
CGTGTAGCAG TGANATGCGT NGATATGCGG AGGAACACCG ATGGCGAAGG CACTCCCCTG 300
GGCCTGCACT GACGCTCATA CACGAANGCG TGGGGAGCAA ACAGTATT             348
```

( 2 ) INFORMATION FOR SEQ ID NO:10:

( i ) SEQUENCE CHARACTERISTICS:
( A ) LENGTH: 348 base pairs
( B ) TYPE: nucleic acid
( C ) STRANDEDNESS: single
( D ) TOPOLOGY: linear ( i i ) MOLECULE TYPE: nucleic acid
( A ) DESCRIPTION: "16S ribosomal DNA"

( i i i ) HYPOTHETICAL: NO ( i v ) ANTI-SENSE: NO ( v i ) ORIGINAL SOURCE:
( A ) ORGANISM: Comamonas acidovorans ATCC No. 15668

( x i ) SEQUENCE DESCRIPTION: SEQ ID NO:10:

```
TACGGAACGA AAANGCTTCT CCTAATACGA GAGGCCCATG ACGGCACCGT AAGAATAAGC  60
ACCGTATANC TACGTGCCAG CAGCCGCGGT AATACGTAGG GTGCGAGCGT TACTCGGTAT 120
TACTGGGCGT AAAGCGTGCG CAGGCGGTTA TGTAAGACAG ATGTGACCTC CCCGGTCTCA 180
NCCTGGGAAC TGCATGTGTG ACTGCATGGC TAGAGTACGG GAGAGGGGGA TCGAATTCCG 240
CGTGTAGCAG TGATATGCGT AGATATGCGG AGGAACACCG ATGGCGAAGG CACTCCCCTG 300
GCCCTGTTCT GACGCTCATA CACGAAAGCG TGGGGAGCAA ACAGTATT             348
```